US010085642B2

(12) United States Patent
Frederick et al.

(10) Patent No.: US 10,085,642 B2
(45) Date of Patent: Oct. 2, 2018

(54) MULTI-MODAL IMAGING OF BLOOD FLOW

(75) Inventors: Blaise Frederick, Belmont, MA (US); Yunjie Tong, Melrose, MA (US)

(73) Assignee: McLean Hospital Corporation, Belmont, MA (US)

( * ) Notice: Subject to any disclaimer, the term of this patent is extended or adjusted under 35 U.S.C. 154(b) by 1259 days.

(21) Appl. No.: 13/701,567

(22) PCT Filed: Jun. 6, 2011

(86) PCT No.: PCT/US2011/039230
§ 371 (c)(1),
(2), (4) Date: Feb. 18, 2013

(87) PCT Pub. No.: WO2011/153521
PCT Pub. Date: Dec. 8, 2011

(65) Prior Publication Data
US 2013/0144140 A1    Jun. 6, 2013

Related U.S. Application Data

(60) Provisional application No. 61/351,703, filed on Jun. 4, 2010.

(51) Int. Cl.
*A61B 5/00* (2006.01)
*A61B 5/026* (2006.01)
(Continued)

(52) U.S. Cl.
CPC .......... *A61B 5/0035* (2013.01); *A61B 5/0042* (2013.01); *A61B 5/0075* (2013.01);
(Continued)

(58) Field of Classification Search
None
See application file for complete search history.

(56) References Cited

U.S. PATENT DOCUMENTS

2004/0254446 A1    12/2004 Miller et al.
2005/0177041 A1    8/2005 Eda et al.
(Continued)

FOREIGN PATENT DOCUMENTS

JP    2003-093390    4/2003
WO   WO 2008147326 A1 * 12/2008 ............. G01R 33/46

OTHER PUBLICATIONS

Strangman, G., "A Quantitative Comparison of Simulatneous BOLD fMRI and NIRS Recordings during Functional Brain Activation", NeuroImage, 2002, vol. 17, pp. 719-731.*
(Continued)

*Primary Examiner* — Tse Chen
*Assistant Examiner* — Joanne Hoffman
(74) *Attorney, Agent, or Firm* — Quarles & Brady LLP

(57) ABSTRACT

The application features methods, devices, and systems for measuring blood flow in a subject. The computer-implemented methods include receiving functional magnetic resonance imaging (fMRI) data that provides information on at least one of volume or oxygenation of blood at one or more locations in a body over a first predetermined length of time. The methods also include receiving near-infrared spectroscopic (NIRS) imaging or measurement data representing at least one of blood concentration or oxygenation at a first portion of the body over a second predetermined length of time. The methods further include deriving, from the fMRI data corresponding to a second portion of the body, a time varying data set representing changes in blood oxygenation or volume or both blood oxygenation and volume at the second portion over the first predetermined length of time and determining, by a computing device, a time delay and a value of a similarity metric corresponding to a part of the spectroscopic imaging data that most closely matches the time varying data set. The time delay represents a difference
(Continued)

between a first time in which blood flows from a third portion in the body to the first portion and a second time in which blood flows to the second portion from the third portion. The value of the similarity metric represents an amount of blood at the second portion. An estimate of a characteristic of at least one of blood flow or blood volume in the second portion at a given time is determined based on the time delay and the value of the similarity metric.

14 Claims, 19 Drawing Sheets

(51) Int. Cl.
    *A61B 5/055*     (2006.01)
    *A61B 5/1455*     (2006.01)
    *A61B 5/02*     (2006.01)
    *A61B 5/0295*     (2006.01)

(52) U.S. Cl.
CPC ...... *A61B 5/02014* (2013.01); *A61B 5/02042* (2013.01); *A61B 5/0261* (2013.01); *A61B 5/0263* (2013.01); *A61B 5/0295* (2013.01); *A61B 5/055* (2013.01); *A61B 5/14551* (2013.01); *A61B 5/4088* (2013.01); *A61B 5/4244* (2013.01); *A61B 5/4312* (2013.01); *A61B 5/4842* (2013.01); *A61B 5/4848* (2013.01); *A61B 5/7203* (2013.01); *A61B 5/7225* (2013.01); *A61B 5/7278* (2013.01); *A61B 5/742* (2013.01); *A61B 5/4064* (2013.01)

(56) References Cited

U.S. PATENT DOCUMENTS

2006/0241374 A1   10/2006  George et al.
2007/0282189 A1*  12/2007  Dan et al. ..................... 600/407

OTHER PUBLICATIONS

Xu Cui, Signe Bray, Daniel M. Bryant, Gray H. Glover, and Allan L. Reiss, "A quantitative comparison of NIRS and fMRI across multiple cognitive tasks", epublished 2010 NIH Public Access Author Manuscript.*

Deepak K. Gupta, George R. McKee, and Raymond J. Fonck, "Dynamic programming based time-delay estimation technique for analysis of time-varying time-delay", Review of Scientific Instruments 81, 013501 (2010).*

T.J. Huppert, R.D. Hoge, S.G. Diamond, M.A> Franceschini, and D.A. Boas, "A tempoeral comparison of BOLD, ASL and NIRS hemodynamic responses to motor stimuli in adult humans", Neuro Image 29, p. 368-382 (2006).*

Angelo Sassaroli, Blaise deB Frederick, Yunjie Tong, Perry F. Renshaw, and Sergio Fantini, "Spatially weighted BOLD signal for comparison of functional magnetic resonance imaging and near-infrared imaging of the brain", NeuroImage 33, p. 505-514 (2006).*

The International Search Report and Written Opinion dated Jan. 11, 2012 for International Application No. PCT/US2011/039230.

* cited by examiner

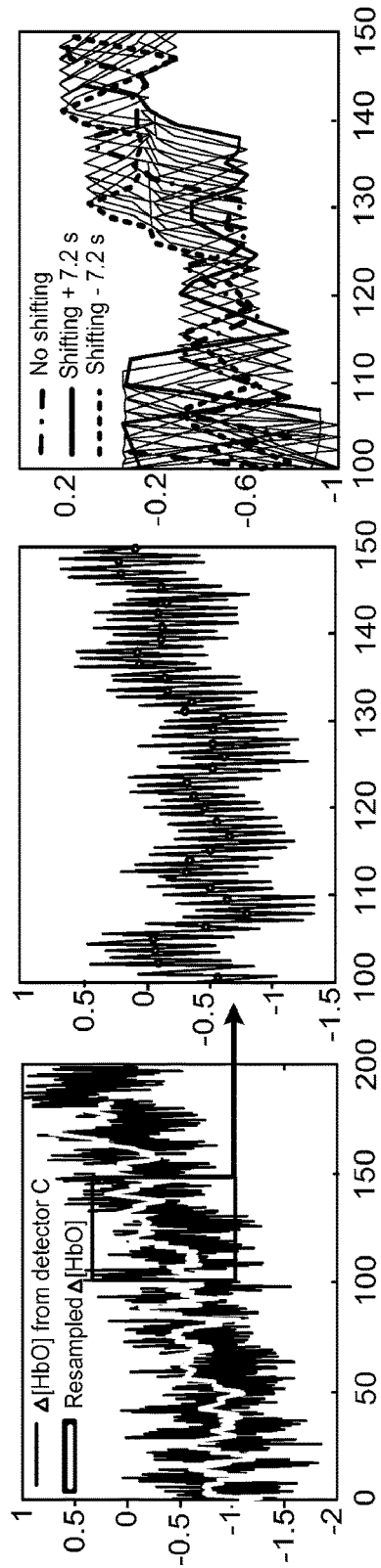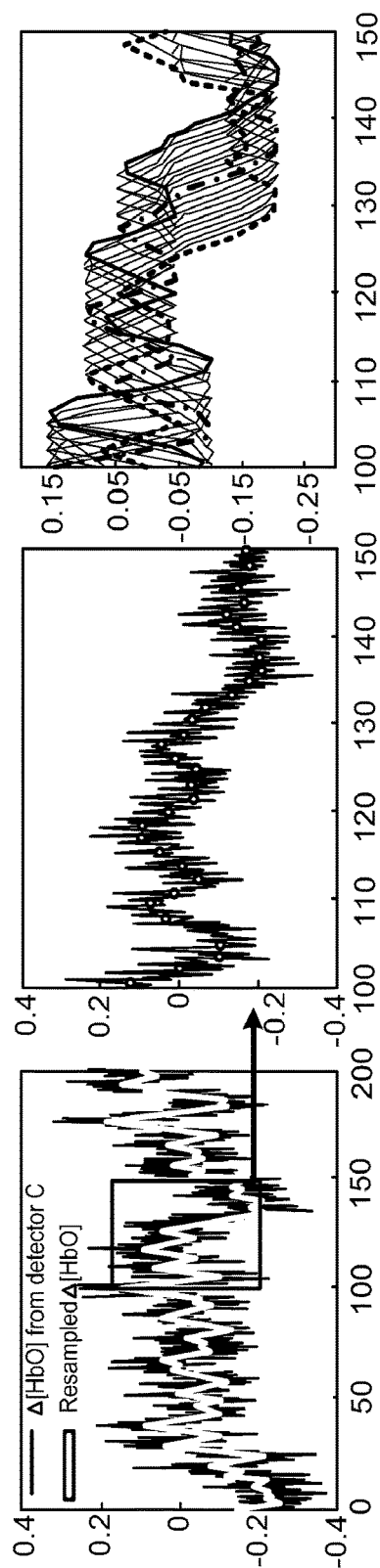
FIG. 6A  FIG. 6B  FIG. 6C
FIG. 6D  FIG. 6E  FIG. 6F

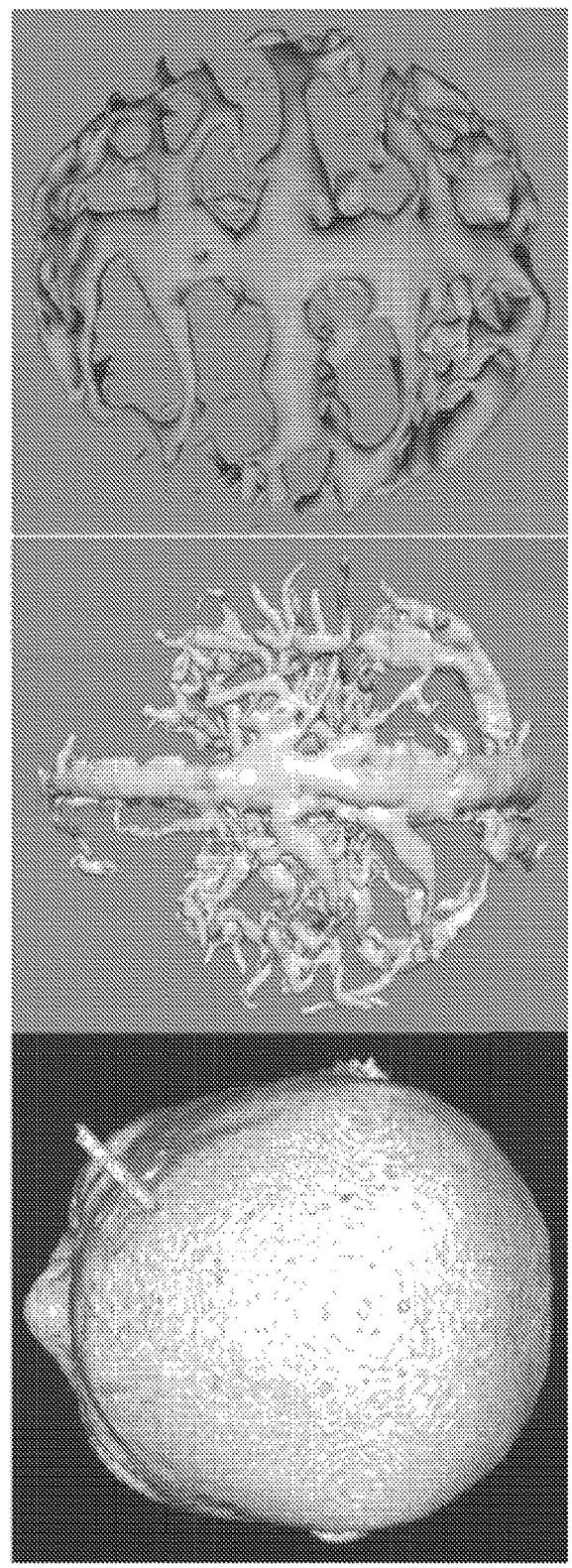

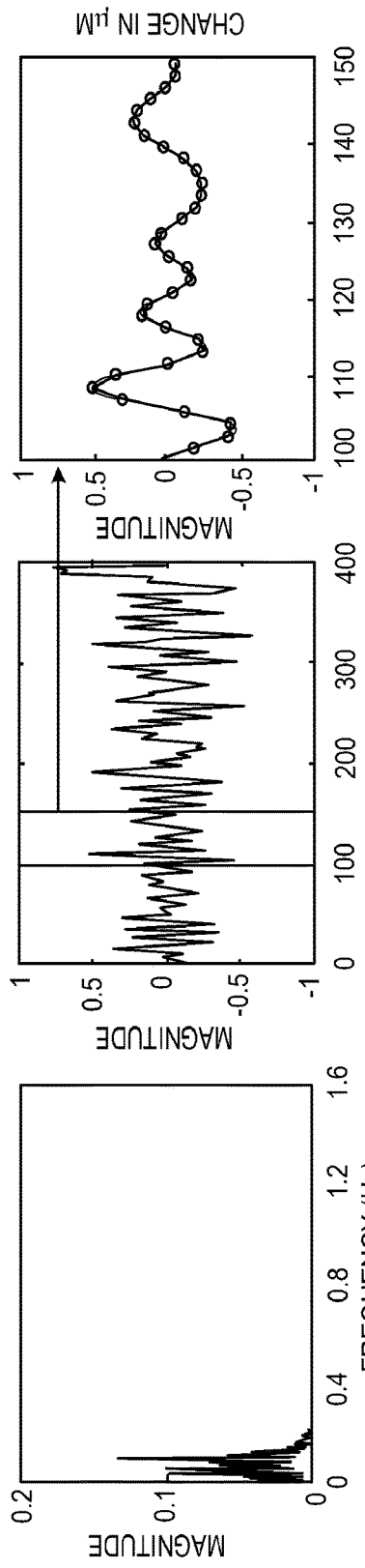
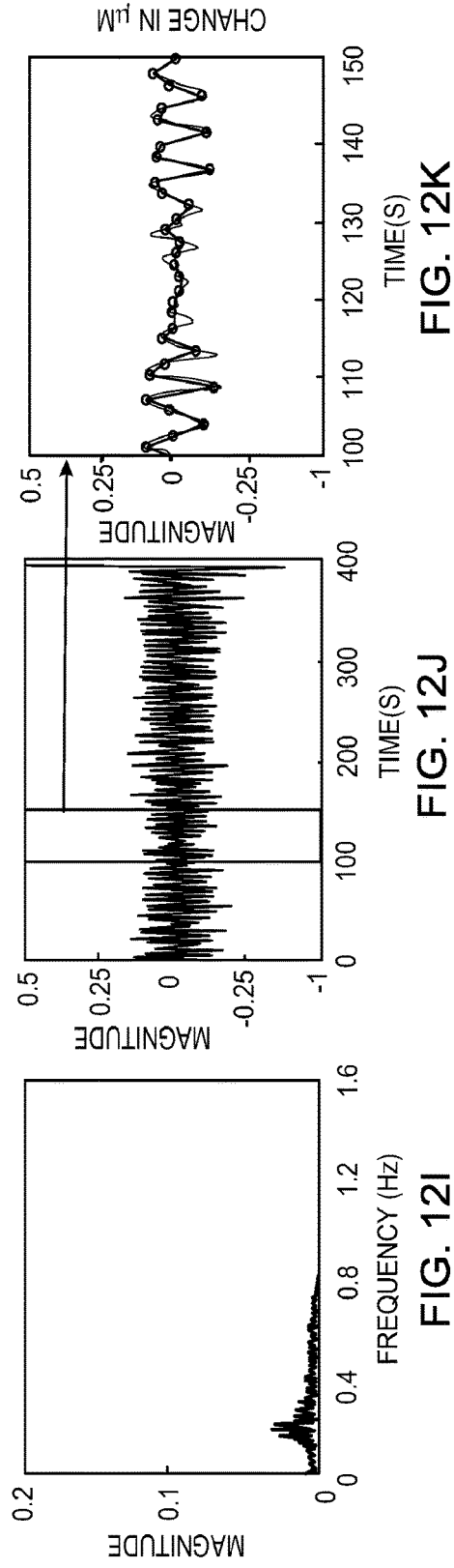

MULTI-MODAL IMAGING OF BLOOD FLOW

CROSS-REFERENCE TO RELATED APPLICATIONS

This application represents the national stage entry of PCT International Application No. PCT/US2011/039230 on Jun. 6, 2011 and claims the benefit of U.S. Provisional Patent Application No. 61/351,703 filed Jun. 4, 2010. The contents of both of these applications are hereby incorporated by reference as if set forth in their entirety herein.

STATEMENT REGARDING FEDERALLY SPONSORED RESEARCH

This invention was made with Government support under Grant Number DA021817 awarded by the National Institutes of Health. The Government has certain rights in the invention.

FIELD OF THE INVENTION

The invention relates to mapping blood flow through an organ of a subject.

BACKGROUND OF THE INVENTION

Measuring blood flow in organs is useful in a variety of diagnostic and therapeutic procedures. Magnetic resonance imaging (MRI) can be used for such measurements. In some cases, blood flow is measured using MRI based methods that use exogenous contrast agents such as gadolinium to track blood through an organ, which can have certain risks. Some MR methods label the inflowing blood using magnetic resonance techniques (e.g., saturation or inversion of carotid blood) using special radio frequency (RF) coils or pulse sequences. Such methods suffer from low sensitivity, low resolution, and a limitation on the duration of time that blood can be tracked due to loss of coherence of tagged blood.

SUMMARY OF THE INVENTION

Blood flowing in a subject's body has natural variations in oxygenation and total hemoglobin level over a range of timescales. The level of oxygenation and total hemoglobin in tissue is governed by various factors including heartbeat, respiration, low frequency fluctuations in blood pressure, and other physiological noise. The present invention, is based, at least in part, on the recognition that if a temporal pattern of oxygenation and total hemoglobin in a volume of blood is detected at a given point in an organ, the flow of the blood can be tracked throughout the organ by detecting substantially the same pattern of oxygenation and total hemoglobin in other parts of the body. Blood oxygenation level-dependent functional MRI (BOLD fMRI) reflects changes in local blood oxygenation levels and volume in various parts of an organ. On the other hand, near-infrared spectroscopy (NIRS) is an imaging modality that tracks temporal changes in oxygenation and total hemoglobin level at a given portion of the body. The present invention is based, at least in part, on the discovery that patterns of oxygenation and total hemoglobin detected using NIRS can be matched with a BOLD fMRI pattern in an area of interest to estimate a time delay that corresponds to the difference in the time in which blood flows to the NIRS measurement point and to the area of interest from another, third point. Further, the degree of match provides information on the amount of blood in the area of interest. This information can be used to map blood flow through the organ.

In a first aspect, the invention features computer-implemented methods for measuring at least one of blood flow and volume in a subject. The methods include receiving functional magnetic resonance imaging (fMRI) data that provides information on at least one of volume or oxygenation of blood at one or more locations in a body over a first predetermined length of time. The methods also include receiving near-infrared spectroscopic imaging or measurement data representing at least one of blood concentration or oxygenation at a first portion of the body over a second predetermined length of time. The methods further include deriving, from the fMRI data corresponding to a second portion of the body, a time varying data set representing changes in blood oxygenation or volume or both blood oxygenation and volume at the second portion over the first predetermined length of time and determining, by a computing device, a time delay and a value of a similarity metric corresponding to a part of the spectroscopic imaging data that most closely matches the time varying data set.

The time delay represents a difference between a first time in which blood flows from a third portion in the body to the first portion and a second time in which blood flows to the second portion from the third portion. The value of the similarity metric represents an amount of blood at the second portion. An estimate of a characteristic of at least one of blood flow or blood volume in the second portion at a given time is determined based on the time delay and the value of the similarity metric.

In a second aspect, the invention features computer-implemented methods for reducing noise in functional magnetic resonance imaging (fMRI) data. The methods include receiving functional magnetic resonance imaging (fMRI) data that provides information on at least one of oxygenation or volume of blood in one or more locations in a body over a first predetermined length of time. The methods also include receiving near-infrared spectroscopic imaging or measurement data representing at least one of blood concentration or oxygenation at a first portion of the body over a second predetermined length of time.

The methods further include deriving, from the fMRI data corresponding to a second portion of the body, a time varying data set representing changes in at least one of blood oxygenation or volume at the second portion over the first predetermined length of time. The spectroscopic imaging data can be separated into a plurality of frequency bands and for each of the plurality of frequency bands, a computing device determines a part of the spectroscopic imaging data that most closely matches the time varying data set derived from the fMRI data from the second portion of the body part. The method also includes identifying a frequency band from the plurality of frequency bands for which the corresponding matching part most closely matches the time varying data set and filtering the fMRI data to exclude the identified frequency band.

In a third aspect, the invention features an apparatus for measuring at least one of blood flow or volume. The apparatus includes a functional magnetic resonance imaging (fMRI) module configured to collect fMRI data from a body of a subject. The fMRI data provides information on at least one of oxygenation or volume of blood at one or more locations in a body of the subject over a first predetermined length of time. The apparatus also includes a near-infrared spectroscopy (NIRS) module configured to collect data representing at least one of blood concentration or oxygenation at a first portion of the body part over a second predetermined length of time. The apparatus further includes a processor that is in communication with the fMRI module and the NIRS module. The processor is configured to derive, from the fMRI data corresponding to a second portion of the body, a time varying data set representing changes in at least one of blood oxygenation or volume at the second portion over the first predetermined length of time. The processor also determines a time delay and a value of a similarity metric corresponding to a part of the spectroscopic imaging data that most closely matches the time varying data set. The time delay represents a difference between a first time in which blood flows from a third portion on the body to the first portion and a second time in which blood flows to the second portion from the third portion. The value of the similarity metric represents an amount of blood at the second portion. The processor is also configured to determine, based on the time delay and the value of the similarity metric, an estimate of a characteristic of at least one of blood flow or volume in the body part at a given time.

In a fourth aspect, the invention features a computer-readable medium storing a computer program for measuring at least one of blood flow or volume. The computer program includes instructions for causing a computer system to receive functional magnetic resonance imaging (fMRI) data that provides information on at least one of volume or oxygenation of blood at one or more locations in a body over a first predetermined length of time. The computer program also includes instructions for causing a computer system to receive near-infrared spectroscopy (NIRS) imaging data representing at least one of blood concentration or oxygenation at a first portion of the body part over a second predetermined length of time. The computer program further includes instructions for causing a computer system to derive, from the fMRI data corresponding to a second portion of the body part, a time varying data set representing changes in at least one of blood oxygenation or volume at the second portion over the first predetermined length of time and determine a time delay and a value of a similarity metric corresponding to a part of the spectroscopic imaging data that most closely matches the time varying data set. The time delay represents a difference in time between a first time in which blood flows from a third portion on the body to the first portion and a second time in which blood flows to the second portion from the third portion. The value of the similarity metric represents an amount of blood at the second portion. The computer program also includes instructions for causing a computer system to determine, based on the time delay and the value of the similarity metric, an estimate a characteristic of at least one of blood flow or volume in the second portion at a given time.

Each of the implementations described above with respect to the first, second, third and fourth aspects of the invention, and other implementations described herein, can include one or more of the following features, individually or in combination.

The fMRI data can be acquired from a plurality of fMRI scans performed over the first predetermined time period and at a predetermined frequency. The second predetermined length of time can include, and can be longer than, the first predetermined length of time. The first portion of the body can include a major blood vessel. The time-varying spectroscopic measurement data can be filtered using a digital or analog filter to reduce noise. The spectroscopic data can be separated into a plurality of frequency bands, which can be compared, individually or together, to the fMRI data.

Estimating the time delay can include dividing the spectroscopic imaging data into a plurality of segments wherein each segment corresponds to a particular time shift, identifying a segment from the plurality of segments that matches the time varying data set derived from the fMRI data from the second portion of the body, and estimating the time delay based on the particular time shift of the identified segment. Each segment of the plurality of segments can be cross-correlated with the time varying data set derived from the fMRI data from the second portion of the body. A peak cross-correlation amplitude can represent the value of the similarity metric. Multiple linear model fits can be performed using the plurality of segments. A first segment from the plurality of segments can partially overlap a second segment from the plurality of segments. The estimated characteristic can be rendered on a display. The estimated characteristic can be an amount of blood a speed of blood. The first portion of the body can at least partially overlap the second portion of the body.

The term "matching," as used herein, refers to calculating a degree of similarity between two data sets. The degree of similarity can be measured, for example, by calculating a cross-correlation between the data sets of or fitting a curve (e.g., via a general linear model analysis) to the datasets.

The term "near-infrared spectroscopy" or "NIRS" as used herein, is a spectroscopic method that uses light between about 650 and about 950 nm to non-invasively probe the concentration and level of oxygenation of hemoglobin in blood. The blood can be flowing through, for example, the brain, muscles, or other tissues in the body.

A "similarity metric," as used herein refers to a metric used for measuring how closely a data set resembles another data set. Examples of similarity metrics include cross-correlation, correlation coefficient, mutual information, sum of absolute differences, sum of squared differences, and root mean squared difference.

The new methods and systems described herein provide numerous benefits and advantages (some of which may be achieved only in some of its various aspects and implementations) including the following. In general, the new methods and systems allow improved and non-invasive measurement of blood flow and/or blood volume. The high spatial resolution of fMRI data can now be used in conjunction with low cost NIRS measurement systems. The invention allows mapping of various parameters related to blood flow such as speed, oxygen concentration, and volume and is useful in various diagnostic and therapeutic procedures. For example, this can be used to measure cerebral perfusion of various parts of the brain.

Some diagnostic uses of the methods and systems described herein include, as non-limiting examples: 1) assessing frontal and/or temporal lobe perfusion in suspected Alzheimer's disease either at a single time or over many months or years to track disease progression or improvement; 2) looking for other perfusion anomalies in various dementias to determine appropriate treatment and/or diagnosis; 3) determining regions of ischemia and/or bleeding in stroke patients, for example, to determine the extent of damage or plan and assess treatment; and 4) to determine cerebrovascular reserve in patients with cerebral artery occlusion or various other chronic circulatory deficits.

The techniques could also be used throughout the body for a number of purposes, for example: 1) assessing perfusion in limbs to determine the degree and character of circulatory deficits resulting from diabetes, coronary artery disease, or other conditions at a single time point or over time to determine disease progression; 2) assessing perfusion in the limbs after treatment for circulatory deficits, such as by balloon angioplasty, to measure treatment efficacy; 3) detecting regions of circulatory enhancement which could be indicative of neoplasms, for example breast, liver or brain tumors; 4) detecting hematomas in the liver; and 5) as a mammography technique to assess changes in breast circulation over time which could give an early indication of breast cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 6A-6F are plots representing examples of temporal changes of the concentrations of oxy-hemoglobin and deoxy-hemoglobin in human blood.

FIGS. 10A-10C are a series of 3-D rendered images of a subject's head (FIG. 10A), a combined z-statistic map in a 3-D rendition (FIG. 10B), and a phase contrast angiogram (FIG. 10B).

DETAILED DESCRIPTION

The methods, devices, and systems described herein can be implemented in many ways. Some useful implementations are described below. The descriptions of implementations of the new methods, devices, and systems do not limit the inventions described in broader terms in the claims.

Multi-Modal Measurements of Blood Flow

Figure 1:
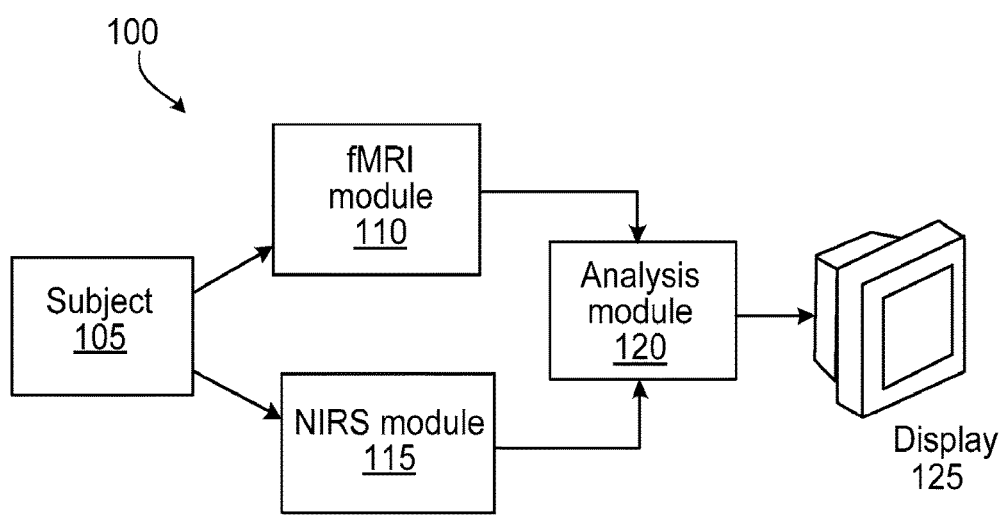
FIG. 1 is a schematic block diagram of a set-up for multi-modal measurement of blood flow.

FIG. 1 shows a system 100 for multi-modal measurement of blood flow. This set-up can be used to measure blood flow in an organ of a subject 105. The system 100 includes a functional magnetic resonance (fMRI) module 110 that captures an fMRI dataset from the subject 105.

The fMRI is a type of specialized MRI scan. In general, fMRI records multiple images sequentially from the brain to detect hemodynamic responses (e.g. change in blood flow or oxygenation) related to neural activity in the brain or spinal cord of humans or other animals. In some cases, fMRI can be used to measure blood oxygen level-dependent (BOLD) contrast, which is the MRI contrast arising from the different magnetic properties of blood oxy-hemoglobin or deoxy-hemoglobin. In general, since neurons do not have internal reserves for glucose and oxygen, an increased neuronal activity may require more glucose and oxygen to be delivered through blood stream rapidly. Hemodynamic response is the process through which blood supplies oxygenated blood for the active neurons at a greater rate than in the area of inactive neurons. This results in a surplus of oxyhemoglobin in the veins of the area and a distinguishable change of the local ratio of oxyhemoglobin to deoxyhemoglobin, which in turn may alter the local image intensity in BOLD fMRI.

Oxy-hemoglobin or oxygenated hemoglobin is diamagnetic while deoxyhemoglobin or de-oxygenated hemoglobin is paramagnetic. The magnetic resonance (MR) signal of blood (or tissue close to blood) is therefore different depending on the level of oxygenation. In general, higher BOLD signal intensities arise from decreases in the concentration of deoxy-hemoglobin. By using MRI sequence parameters which make image intensity sensitive to changes in magnetic susceptibility, one can assess changes in BOLD contrast. These changes can be either positive or negative depending upon relative changes in cerebral blood flow (CBF), cerebral blood volume (CBV) and/or oxygen consumption. Statistical methods can be used on BOLD fMRI signals to determine which areas of an organ, e.g., the brain, are more active than others.

In general, fMRI can be used for tracking blood through an entire organ and therefore fMRI data sets generally have good spatial coverage. In some implementations, multiple fMRI scans are acquired to achieve more meaningful statistical results or extended spatial coverage. The duration over which fMRI scans for an organ are acquired is usually at least several times longer than the time taken by blood to pass through the organ. For example, blood takes around 10 seconds to circulate through a human brain. Therefore, while acquiring fMRI scans of a human brain, the acquisition time is adjusted accordingly.

BOLD fMRI scans are typically acquired using rapid volumetric acquisition of images. Voxels in the resulting image typically represent small cubes of tissue, e.g., about 2-4 millimeters on each side in humans. In some implementations, high magnetic fields and multichannel radiofrequency (RF) reception can be used for increased spatial resolution, e.g., on the order of millimeters, and/or for better measurement sensitivity. The frequency of acquiring the fMRI scans are in general selected to be fast enough to track blood adequately through the organ of interest. In the case of BOLD fMRI, the frequency is selected such that fluctuations of interest in the blood oxygen level are adequately sampled. In general, the frequency of the fMRI scans is selected in accordance with the Nyquist rate, i.e., at least twice the frequency of the projected fluctuation rate. However, the methods and systems described herein can also be used with lower sampling rates.

System 100 also includes a near-infrared spectroscopy (NIRS) module 115. NIRS is an in vivo spectroscopic method that uses the red/near-infrared region of the electromagnetic spectrum (e.g., from about 650 nm to 900 nm). NIRS is a non-invasive, low-cost functional brain imaging modality that measures hemoglobin concentration and oxygenation at high temporal resolution (e.g., ~10 ms) in an organ of interest, e.g., the cerebral cortex of the human brain. In some implementations, the NIRS module 115 includes a source, a detector, and a dispersive element (such as a prism or a diffraction grating) to allow the intensity at different wavelengths to be recorded. In some implementations, the NIRS module can also include a Fourier transform-based instrument and an interferometer. In general, the spectrum of energy from the source can be measured at the detector via reflection or transmission through the dispersive element.

In some implementations, the source includes a broadband source such as an incandescent or quartz halogen light bulb. Light-emitting diodes (LEDs) or lasers can also be used as a source. The type of detector, in general, depends on the range of wavelengths that are detected. For example, silicon-based CCDs are suitable for the shorter end of the near-infrared (NIR) range. For higher ranges, InGaAs and PbS devices are generally more suitable. In some implementations, for example, in diode array (DA) NIRS instruments, both silicon-based and InGaAs detectors can be used in the same instrument. Photomultiplier tubes (PMT's) are also commonly used. In some cases, multiple detectors are arranged in the NIRS module 115 in a one-dimensional (1D) array or a two-dimensional (2D) array. In general, the NIRS module sequentially acquires multiple measurements at different narrow wavelength bands.

System 100 further includes an analysis module 120 that analyzes the data sets acquired by the fMRI module 110 and the NIRS module 115 to measure blood flow in an organ of interest from the multi-modal data. In general, the analysis module 120 includes a computing device with a processor that can be configured to analyze the multimodal data. The system can also include a display device 125 to visually render the analysis results. For example, the analysis results may yield a series of cerebral blood flow (CBF) maps or cerebral blood volume (CBV) maps that are rendered on the display 125 as a series of images or video.

Signal Processing

Figure 2:
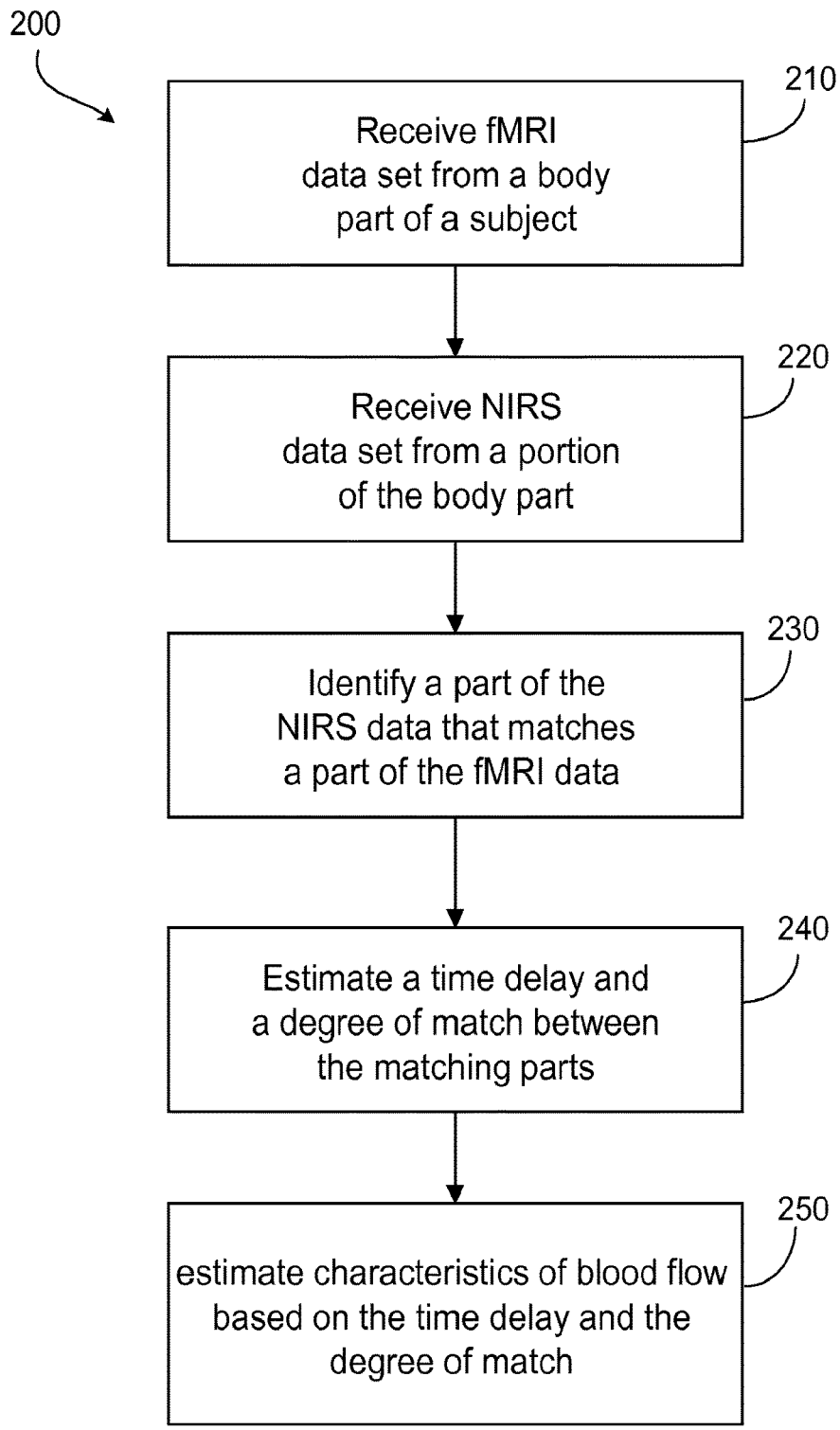
FIG. 2 is a flow diagram depicting an example of a sequence of operations for measuring blood flow.

FIG. 2 is a flow diagram 200 that represents exemplary operations or methods to measure characteristics of blood flow from multi-modal data. In general, the correspondence between the fMRI and NIRS data sets can be characterized using data from a predetermined frequency band. For example, low frequency oscillations (LFOs), characterized by frequencies in the range of approximately 0.01 to approximately 0.1 Hz, are commonly observed in NIRS and fMRI data. In some cases, LFOs may represent one or more types of neuronal signaling, systemic hemodynamics, and/or cerebral vascular auto-regulation processes. The operations depicted in flow diagram 200 combine the advantages of the high spatial resolution offered by fMRI (e.g., ~3 mm) and the high temporal resolution offered by NIRS (e.g., ~80 ms) to quantitatively assess temporal relationships between oscillations in characteristic frequency bands (e.g., the LFOs observed at different spatial locations in the fMRI data. In some implementations, the temporal relationship indicates that the origin of a large proportion of the characteristic oscillations (e.g., LFOs) is independent of physiological activity such as baseline neural activity. In some implementations, the spatio-temporal pattern of characteristic oscillations (e.g., LFOs) detected by NIRS and fMRI is an indicator of blood flow dynamics through an organ of interest.

The methods include receiving (step 210) an fMRI data set from a body part of a subject. The body part may include one or more organs such as a brain or a breast. In general, the fMRI data set is acquired with a repetition frequency fast enough to track blood through the body part or organ of interest and adequately sample blood oxygen fluctuations. The fMRI data is acquired over a predetermined time such that data on blood flow through the entire organ is captured. In general, the fMRI data set is a series of spatio-temporal images that represent the blood oxygen fluctuations in different parts of the body part over a range of time. For example, when a series of images (e.g., comprising multiple voxels each) are available for a given portion of the body part (e.g., represented by a particular voxel), the time variation of blood oxygen fluctuations at that portion can be derived from the series of images. Such time varying data derived from the fMRI data is often referred to as a time course of the fMRI data. Deriving such time courses may include additional signal processing steps such as registration of the images with each other.

The methods also include receiving (step 220) an NIRS data set from a particular portion of the body part. In general, the particular portion is a region through which a large amount of blood flows. For example, if the body part of interest is the brain, the NIRS data set can be acquired by placing a set of probes in a prefrontal area of the head (which will monitor the blood flow at a portion of the cortex or in the surrounding vessels). In some implementations, the NIRS data set can be acquired via measurements of blood as it passes through a large vessel such as the carotid artery or the jugular vein. In some implementations, the NIRS data set can be acquired through measurements performed at other portions of the body, for example at a fingertip or on a toe. In general, NIRS measurements are affected by oxygenation and/or by the amount of blood passing through the portion monitored by the NIRS probes. Therefore, the NIRS data set usually includes a time varying representation of blood oxygen fluctuations for a predetermined amount of time. Even though the NIRS data set is usually referred to as NIRS imaging data, the NIRS data set can include any one dimensional or two dimensional time varying data that represents blood oxygen and/or volume fluctuations. The NIRS data set acquisition is usually started at a predetermined time before starting the fMRI data set acquisition and is continued for a predetermined time after the fMRI acquisition has ended. This is to allow for comparing time shifted segments of the NIRS data with the fMRI data.

The methods further include identifying (step 230) a part of the NIRS data that matches a part of the fMRI data. The part of the fMRI data that the NIRS data is matched to is usually a time course derived for a particular portion of the fMRI data (e.g., a voxel or collection of nearby voxels). Such matching can include, for example calculation of a similarity metric such as cross-correlation, the value of which represents how closely the oxygen fluctuations in a part of the NIRS data resembles the oxygen fluctuation in the part of the fMRI data at a certain time lag or delay between the two. In some implementations, the matching can include a general linear model (GLM) analysis of the fMRI data using a single time-lagged version of the NIRS signal as a regressor of interest. This procedure can be repeated several times over a range of time lags. In some implementations, additional signal processing steps are performed prior to comparing the fMRI and NIRS data. For example, either or both of the fMRI and NIRS signals can be filtered to remove artifacts and unwanted components such as measurement noise and probe movement artifacts. In some implementations, one or more of the fMRI and NIRS signals can be filtered to select a range of frequencies that carries reliable information on the blood flow and/or blood oxygenation.

For example, the NIRS signal is frequently dominated by LFOs, e.g., frequencies between 0.009 and 0.15 Hz, especially when signals associated with brain activation tasks are relatively small. In such task activation studies, the LFO is typically reduced by averaging the response of many repetitions of a stimulus, and/or by high pass filtering. Similarly, LFOs are commonly observed in BOLD fMRI, e.g., during studies of task activation and resting-state activity. Therefore, in cases where LFOs are of interest, such as in "resting-state" studies, the fMRI and/or NIRS signals may be filtered to isolate frequency bands that contain the LFOs. In some implementations, the filtering is done to reduce the effect of blood oxygen fluctuations due to other physiological processes such as heartbeat and respiration. The corresponding frequency bands are sometimes referred to as the cardiac band and the respiratory band, respectively. In some implementations, frequencies representing the cardiac waveform (e.g., 0.5-3.0 Hz, depending on the subject or the subject's condition) also carry useful information. In some cases, these frequencies are aliased in the fMRI data which requires additional processing. In some cases, aliasing can be avoided by making the fMRI repetition frequency sufficiently fast (e.g., 1-6 Hz), in accordance with the frequency band of interest.

Matching the fMRI data with the NIRS data involves deriving a time course from the fMRI data of a particular portion (e.g., at a specific voxel or group of voxels) of the body part and determining if one or both of the oxygenation and volume fluctuations in any part of the NIRS signal are substantially similar to corresponding fluctuations in the time course. In some implementations, this involves calculating values of a similarity metric between the time course and the time shifted versions of the NIRS signal over a range of time shifts. The similarity metric can include, for example a cross-correlation, or a general linear model (GLM) fit. In some implementations, the range of time delays is selected to be long enough to cover the difference in time it would take blood to propagate to the NIRS probe location and the particular portion of interest from some source location. In general, a peak is observed when the time shifted NIRS signal substantially matches the time course. In some cases, the shape of the time course can represent a global blood oxygenation pattern that travels through the entire organ.

In some implementations, matching an fMRI time course and the NIRS signal is done by performing multiple general linear model fits using versions of the NIRS signal advanced or delayed in time. In some cases, higher order models may also be used. In some implementations, the matching is done by cross-correlating the NIRS signal and the fMRI time course to determine the degree of correlation as a function of time shift of the NIRS signal. In general, cross-correlation is a measure of similarity of two waveforms as a function of a time-lag applied to one of them. Cross-correlation is commonly used to search for a known short signal within another signal of a longer duration. In this case, the NIRS signal is the longer signal and the fMRI time course is the known short duration signal. In some implementations, the matching may also be done by filtering the NIRS signal using a matched filter wherein the NIRS signal is convolved with a time reversed version of the fMRI time course. In some implementations, other measures of similarity including, for example, sum of squared differences, sum of absolute differences, root mean squared difference etc. can be used as metrics in matching the NIRS data to the fMRI time course.

The methods further include estimating (step 240) a time delay and a degree of match if a part of the NIRS signal is detected to match the fMRI time course. In general, the amount of time shift of the NIRS signal corresponding to the matching point (e.g. a cross-correlation peak) represents the time delay. In some implementations, the peak cross-correlation amplitude represents a degree of match. In case of curve fitting (e.g., in GLM analyses), the degree of match is represented by how well a curve fits a given data set at a given time shift.

The methods also include estimating (step 250) characteristics of blood flow and/or volume based on the estimated time delay and the degree of match of one or more NIRS signals. The characteristics of blood flow may include, for example, an amount of blood in the given portion and a speed of blood at the given portion. In general, the degree of match is substantially proportional to the amount of blood and the time delay represents the difference in time needed for the blood to travel from some common source location to the NIRS probe location and the location or portion corresponding to the fMRI time course. The blood flow speed can therefore be calculated from the time delay information. By selecting appropriate ranges of time delay and combining (e.g., by summation or fitting) the data from multiple time delays, a spatially resolved estimate of a characteristic, e.g., amount of blood in a given location at a given time can be generated. By changing the ranges of delays used, arterial, capillary, or venous blood can be emphasized. For example, a signal appearing early on may correspond to arterial blood entering the brain, and a signal at intermediate delays may represent blood in the capillaries and perfusing tissue. Similarly, a signal at the latest delay times may correspond to blood in the draining venous system. In some implementations, the spatially resolved estimates can be visually rendered, e.g. as an image or video.

In some implementations, several fMRI time courses (corresponding to various locations within an organ) are matched with the NIRS signal and the blood flow characteristic is estimated for the different locations. In some implementations, missing locations (or voxels) can be interpolated to complete an estimate for the entire organ.

In some implementations, the time shifts corresponding to the fMRI time courses at various locations can be used to align the signals to a common time, and the shifted time courses can be summed to generate a new, refined estimate of the global blood oxygenation signal. In such cases, steps 230 to 250 can be repeated to further refine the estimate of the blood flow characteristics.

NIRS can be used to measure changes in blood parameters including, for example, oxyhemoglobin concentration, deoxyhemoglobin concentration, and total hemoglobin concentration. In some implementations a single NIRS measurement is used to match the fMRI time courses. In some implementations, multiple NIRS measurements are matched to the fMRI signal, and the results are combined to give more accurate estimates of blood flow, volume, or oxygenation changes.

Removing Physiological Noise

Figure 3:
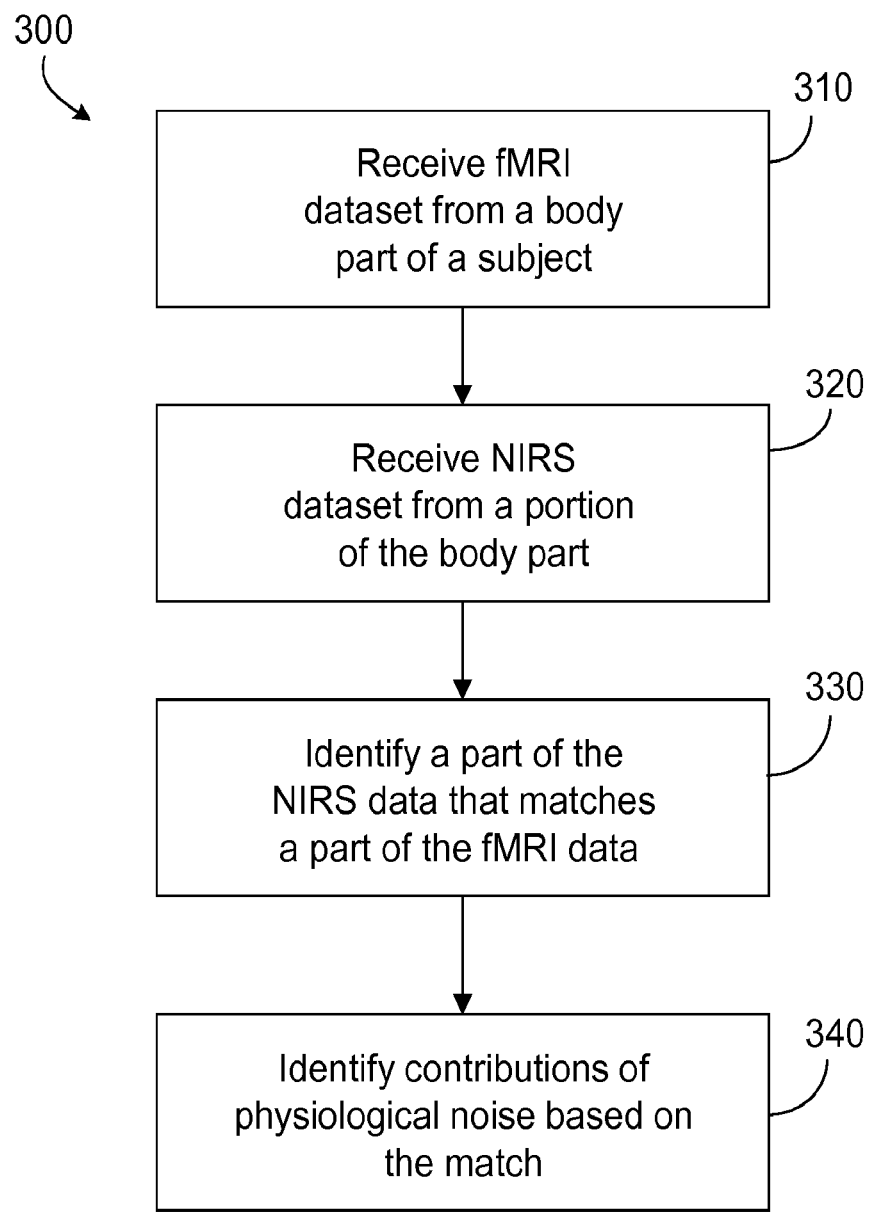
FIG. 3 is a flow diagram depicting an example of a sequence of operations for reducing physiological noise in an fMRI image.

FIG. 3 is a flow diagram 300 that represents exemplary operations or methods to remove physiological noise from BOLD fMRI signals. The methods include receiving (step 310) a fMRI data set from a body part of the subject, receiving (step 320) a NIRS data set from a portion of the body part and identifying (step 330) a part of the NIRS data that matches a part of the fMRI data. In some implementations steps 310, 320, and 330 are substantially same as the steps 210, 220, and 230, respectively, as described with reference to FIG. 2.

The methods also include identifying (step 340) contributions of physiological noise based on the match. For example, in case a match is found, the matching portion of the waveforms corresponding to oxygenation variations propagating through the organ, as described above, may be considered to be non-neuronal, and are confounds (or undesired signals) in detecting of neuronal activity. The matching signals identified through the procedure described in the flowchart 200 can be removed from the BOLD fMRI data set to improve interpretation of the fMRI data as an indicator of neuronal activity. The primary sources of confounding noise in BOLD fMRI data are, in general, due to cardiac and respiratory effects, low frequency oscillations in blood pressure, and non-task related neural activity. Effects due to cardiac noise in particular can be problematic, because these effects are aliased in the recorded data due to relatively low sampling frequencies used for BOLD fMRI acquisition. In some implementations, noise in BOLD fMRI signals can be estimated via direct measurement of global flow and oxygenation fluctuations effects using NIRS, as described above. In other implementations, NIRS can be used to measure changes in concentration in oxy-hemoglobin $\Delta[HbO]$, deoxy-hemoglobin $\Delta[Hb]$, and total hemoglobin $\Delta[tHb]$, at high temporal resolution (6-20 Hz), which allows un-aliased sampling of respiratory and cardiac effects. These measurements can then be used to generate confound regressors by calculating the noise that these signals would generate when undersampled at the BOLD acquisition frequency.

For example, the $\Delta[HbO]$ and $\Delta[Hb]$ signals calculated using NIRS can be filtered into various spectral bands, including: a "cardiac band" (e.g., 0.7-4.5 Hz), a "respiratory band" (e.g., 0.2-0.6 Hz), a "low frequency band" (e.g., 0.05-0.15 Hz), and a "very low frequency band" (e.g., 0.0-0.03 Hz). In some implementations, these signals can be resampled to the fMRI sampling rate, e.g. to account for the variation in sample time for different slices in an image stack, orthogonalized with respect to a task regressor, and added in various combinations as regressors to a general linear model (GLM) analysis. Results such as z-statistic maps can be calculated for all regressors and the best regressor (for example, corresponding to the highest z-statistic value) chosen as a noise estimate. The z statistic has a normal distribution with a mean of zero and a standard deviation of one. Therefore, if the mean and standard deviation for a population is known, a z-statistic can be calculated from a raw value.

In general, concurrently acquired NIRS data identifies a substantial fraction of BOLD fMRI noise, and allows more accurate estimates of task related activations in BOLD fMRI data. Measuring oxygenation fluctuations directly in the brain avoids the need to calculate these effects from physiological waveforms measured outside of the brain.

System Overview

Figure 4:
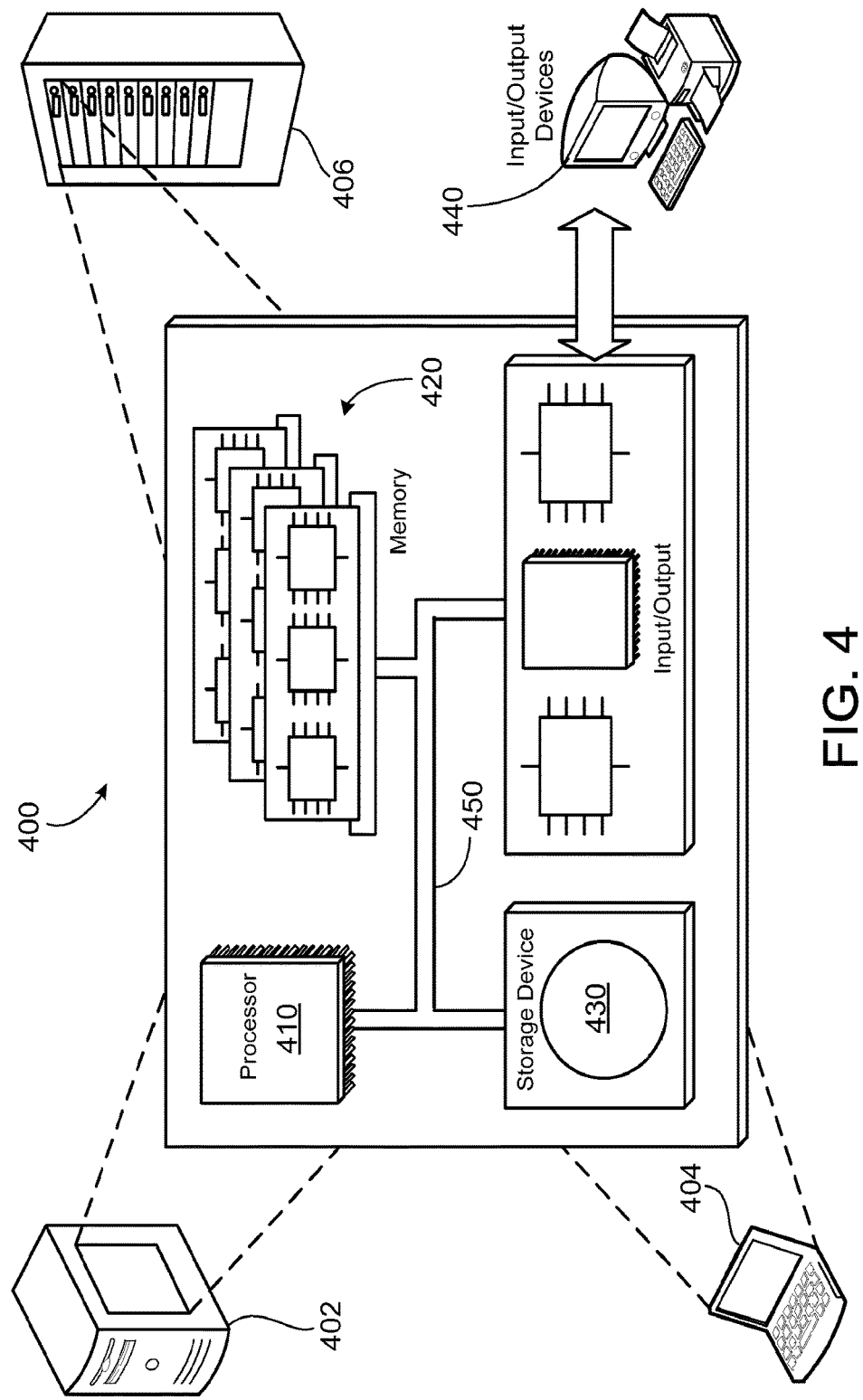
FIG. 4 is a schematic diagram of a computing device and system.

FIG. 4 is a schematic diagram of a computer system 400. The computer system 400 can be implemented as a part of different computing devices such as a desktop computer 402, a laptop computer 404 or a server 406. The system 400 can be used for the operations described in association with any of the computer-implemented methods described herein, according to one implementation. For example, the computer system 400 can be a part of the analysis module 120 and display 125 described with reference to FIG. 1. The analysis module 120 and the display 125 can communicate with parts of the system 400 to perform the operations described herein.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In some implementations, the memory 420 is a computer-readable medium and can include volatile memory and/or non-volatile memory. The storage device 430 and memory 420 are tangible non-transitory media that can store computer readable instructions and/or data.

The storage device 430 is capable of providing mass storage for the system 400. In one implementation, the storage device 430 is a computer-readable medium. In various different implementations, the storage device 430 may be a floppy disk device, a hard disk device, an optical disk device, a tape device, a solid-state storage device, or some other technology.

The input/output device 440 provides input/output operations for the system 400. In some implementations, the input/output device 440 includes a keyboard and/or pointing device. In some implementations, the input/output device 440 includes a display unit for displaying graphical user interfaces.

The features described herein can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both.

Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display), or OLED (organic light emitting diode) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 410 carries out instructions related to a computer program. The processor 410 may include hardware such as logic gates, adders, multipliers and counters. The processor 410 may further include a separate arithmetic logic unit (ALU) that performs arithmetic and logical operations.

Methods of Use

The methods and systems described herein can be used to generate blood flow maps such as cerebral blood volume (CBV) maps and cerebral blood flow (CBF) maps. Such blood volume and blood flow maps can also be generated for other body parts. Frequency bands that carry the most meaningful information for the generation of such maps can also be identified.

For example, the methods and systems described herein can be used to remove physiological noise from BOLD fMRI signals. The NIRS signal, with appropriate time delays, is used for estimating contributions of non-neuronal sources to the fluctuations in BOLD fMRI time courses. The NIRS signals provide measures of changes in levels of total hemoglobin, oxy-hemoglobin and deoxy-hemoglobin and therefore provide waveforms that closely match the source of physiological noise in BOLD fMRI.

The methods and systems described herein can be used for various purposes. In some implementations, tracking blood flow in a particular body part or organ can be used in determining progress or recession of a particular condition. For example, the methods and systems described herein can be used for assessing frontal and/or temporal lobe perfusion in suspected Alzheimer's disease. Measurements can be taken either at a single time or over a period of time (e.g. several months or years) to track disease progression or improvement. In some implementations, the methods and systems described herein can also be used to detect perfusion anomalies in various dementias. Detection of such perfusion anomalies can be used to determine appropriate treatment and/or diagnosis.

In some implementations, the methods and systems described herein can be used in assessing damage to the brain or other organs, such as in determining regions of ischemia and/or bleeding in the brain in stroke patients, for example, to determine the extent of damage or to plan and assess treatment. Similarly, measuring or tracking blood flow also can be used to determine cerebrovascular reserve in patients with cerebral artery occlusion or various other chronic circulatory deficits.

The methods and systems described herein can also be used for other purposes such as for assessing perfusion in limbs to determine the degree and character of circulatory deficits resulting from diabetes, coronary artery disease, or other conditions at a single time point or over time to determine disease progression. In some implementations, the methods and systems described herein can be used for assessing perfusion in the limbs after treatment, such as by balloon angioplasty for circulatory deficits, to measure treatment efficacy. In some implementations, regions of circulatory enhancements can also be detected that, in turn, could be indicative of neoplasms, for example breast, liver, or brain tumors. Tracking and/or measuring blood flow also can be used for detecting hematomas in the liver, or as a mammography technique to assess changes in breast circulation over time, which could give an early indication of breast cancer or be used to track treatment efficacy.

All of these methods can be carried out by those of skill in the relevant fields using the methods and systems described herein.

EXAMPLES

The inventions described herein are further described in the following examples, which do not limit the scope of the invention described in the claims.

Example 1

In this example, the high temporal resolution of NIRS (about 80 ms) was combined with the high spatial resolution of fMRI (about 3.5×3.5×4 mm) to investigate the physiological origin of LFOs detected by both modalities in human brain during a resting state of a subject. The goals of the resting state study were: 1) to examine the temporal and spatial characteristics of LFOs as measured with NIRS; 2) to determine the spatial extent of NIRS LFO in brain; and 3) to investigate temporal changes in the spatial patterns of LFO signal (identified by NIRS) throughout the brain in the BOLD fMRI data.

Both NIRS and BOLD fMRI signals are sensitive to blood-oxygenation-related changes in the brain and both are able to accurately sample the low frequency band (<0.1 Hz), in general, there exists a strong temporal correlation between measurements of low-frequency physiological processes obtained using both techniques simultaneously. Conversely, these two imaging modalities have different physical and instrumentation bases, and therefore typically there is no correlation of instrumentation noise or image artifacts between the two imaging modalities. The correlated components of NIRS and BOLD fMRI datasets are typically related to biological/physiological signals from the tissue under study. The multi-modal processing strategy can therefore be used to characterize low-frequency physiological signals without contamination from instrumental noise and artifacts.

In this example, the NIRS signal was used as a regressor for BOLD fMRI analysis, as a method of characterizing (and removing) BOLD fMRI noise. Further, simultaneous processing of NIRS and BOLD fMRI allowed for measuring the effect of time delay on the correlation between the two modalities.

The time varying NIRS LFO signal from a cortical region was used a reference signal or a regressor in a general linear model (GLM) analysis of the concurrently acquired BOLD fMRI dataset. The high spatial resolution and full brain coverage of fMRI allowed investigating how well the NIRS signal correlates with BOLD fMRI data not only in the region covered by both modalities, but throughout the brain. A large number of voxels in which BOLD activation is correlated with LFO measured by NIRS were visualized. The BOLD voxels that have a high temporal correlation with the NIRS reference signal, in general, provide an indication of the spatial extent and location of the brain areas associated with the NIRS LFO signal, and can also provide insight into the physiological, hemodynamic, and/or functional source of the NIRS signal. By also considering the effect of time delay on the degree of correlation between the modalities, it was determined how these correlations change in time, along with the spatial pattern of the change.

An analysis of simultaneously acquired NIRS and BOLD-fMRI data was performed where the BOLD data showed significant correlations to the LFOs as modeled by the NIRS waveform (in widespread areas throughout the brain). Furthermore, by applying a range of time shifts (both advanced and delayed in time) to the NIRS reference signal, the BOLD-measured LFOs were detected to travel temporally through the brain in a manner that suggested a hemodynamic rather than neuronal origin, and a global rather than a regional character.

Protocol

Concurrent NIRS and fMRI resting state studies were conducted on six healthy volunteers during a resting state acquisition (4 males, 2 females, aged 28.0±4.69 years). During the experiment, the participants were asked to lie quietly in the scanner with their eyes open while fMRI and NIRS data were recorded. During this time, the subject viewed a gray screen with a central fixation point.

fMRI Acquisition and Physiological Monitoring

All fMRI data were acquired on a Siemens TIM Trio 3T scanner (Siemens Medical Systems, Malvern, Pa.) using a 12-channel phased array head matrix coil. A high-resolution anatomic image set was acquired for slice positioning and co-registration of the functional data (T1 weighted multi-echo MP-RAGE3D), resolution (Right-Left (RL), Anterior-Posterior (AP), Superior-Inferior (SI)) of 1.33×1×1 mm, Inversion time (TI)=1,100 ms, Repetition time/Echo time 1 and 2 (TR/TE1,TE2), Field of View (FOV)=171×256×256 mm, 128×256×256 pixels, 2×GRAPPA, total imaging time 4 min 32 sec). This was followed by the resting state scan (2 dummy shots, 260 time points, TR/TE=1500/30 ms, flip angle 75 degrees, matrix=64×64 on a 220×220 mm FOV, 29 3.5 mm slices with 0.5 mm gap parallel to the AC-PC line extending down from the top of the brain, Gene-Realized Auto-calibrating Partially Parallel Acquisition (GRAPPA) acceleration factor of 3).

Physiological waveforms (pulse oximetry and respiratory depth) were recorded using the scanner's built-in wireless finger-tip pulse oximeter and respiratory belt. After the completion of the fMRI acquisition, 3D velocity encoded phase contrast images were acquired to map the blood vessels in the head (1 slab, aligned with the AC-PC plane, 160 0.9 mm slices/slab, 0.8×0.8 mm resolution in the readout (AP, FOV=200 mm) and phase encode (RL, FOV=150 mm) directions, velocity encoding 30 cm/s, total acquisition time 5:55).

NIRS Acquisition

Figure 5:
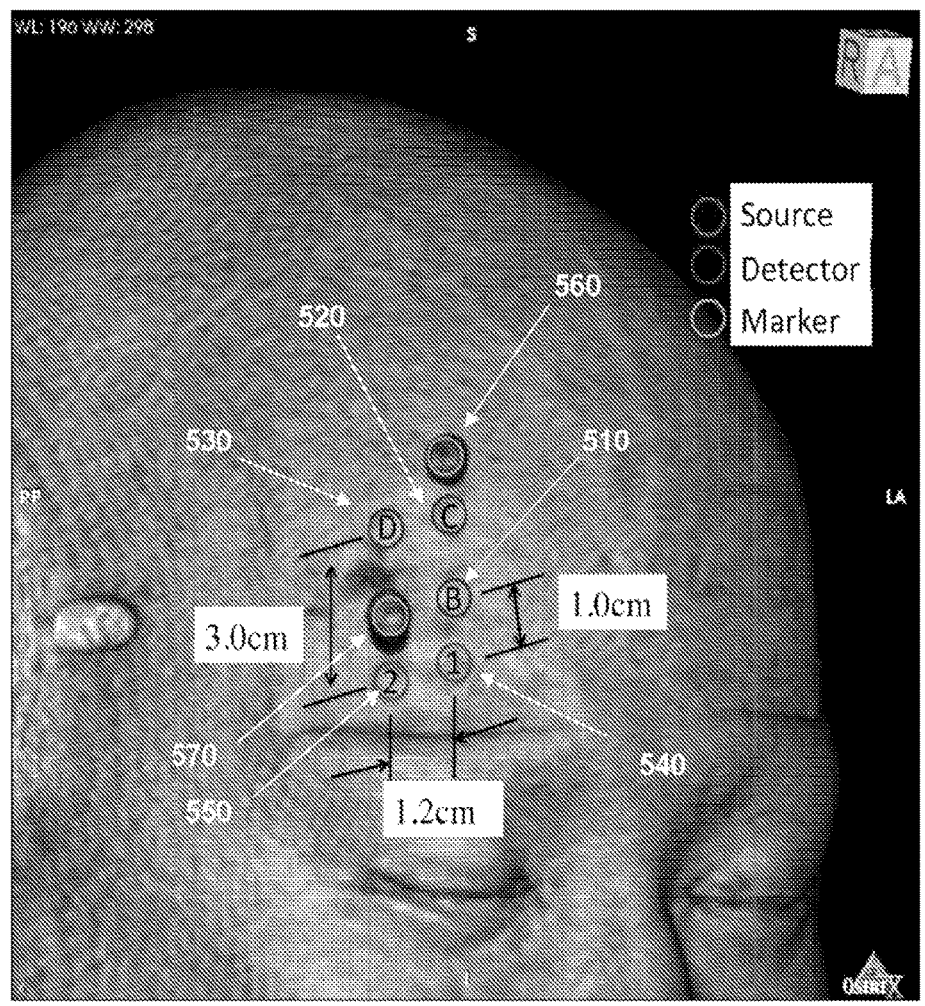
FIG. 5 is a schematic representation that shows an example of positions of NIRS probes on a human head.

An MRI compatible NIRS probe, with three collection points 510, 520, and 530 and two illumination optical fibers 540 and 550, with source-detector distances of 1 or 3 cm was used. The probe arrangement on a patient is shown in FIG. 5. The probe was placed over the right prefrontal area of each participant (roughly between Fp1 and F7 in the 10-20 system) and held in place by an elastic band around the head. 10-20 is a coordinate system defined on the scalp for placing NIRS probes using external landmarks (e.g., ear canals and the bridge of the nose). Fp1 and F7 are two standard points on the frontal lobe that specify the probe placements. The position of the probe was chosen due to its easy accessibility (no hair) and relatively short distance from the scalp to the cortex (11-13 mm on average) in this area. The probe had embedded MRI visible markers 560 and 570 to identify the probe location on the anatomic MRI image.

Each illumination fiber 540 and 550 delivered light from two laser diodes emitting at wavelengths of 690 and 830 nm. The laser diodes and three optical detectors (photomultipliers tubes, Hamamatsu Photonics R928) were housed in a near-infrared tissue imager (Imagent, ISS, Inc., Champaign, Ill.), which was placed in the MRI control room. Three optical paths were formed: one of length 1 cm between the source 540 and the detector 510, one of length 3 cm between the source 540 and the detector 520 and a third one of length 3 cm between the source 550 and the detector 530. The two optical collection points or detectors 520 and 530, which were 3 cm away from their corresponding laser sources 540 and 550, respectively, were labeled C and D. The detector 510 was labeled B. The optical probe and the Imagent instrument were connected by 10 m long optical fibers. The sampling rate of NIRS data acquisition was 12.5 Hz. fMRI data was collected for 6 minutes 30 seconds; NIRS data was recorded continuously during this time as well as for several minutes before and after the fMRI acquisition.

Each pair of raw NIRS time courses (690 and 830 nm data) were converted into two time courses representing temporal changes of the concentrations of oxy-hemoglobin and deoxy-hemoglobin according to a differential path length factor method using a MATLAB® program (The Mathworks, Natick, Mass.). The time courses of differential changes in oxy-hemoglobin ($\Delta[HbO]$) and differential changes in deoxy-hemoglobin ($\Delta[Hb]$) measured with NIRS were then anti-aliased and down-sampled to the fMRI acquisition frequency of 0.67 Hz (1/1.5 s). FIGS. 6A and 6D show the temporal traces of $\Delta[HbO]$ and $\Delta[Hb]$, respectively, along with the corresponding resampled data. The down-sampled $\Delta[HbO]$ data, as well as the down-sampled $\Delta[Hb]$ data were later used as regressors in the general linear model (GLM) analysis of the BOLD data. In order to account for any possible time misalignment between the NIRS and BOLD fMRI data, a range of time shifts were added to the NIRS signal prior to resampling. A positive time shift value meant that the resampled waveform corresponds to events that happened prior to the time the NIRS data was recorded. 21 time shift values, covering the range of −7.2 s to +7.2 s with respect to the unshifted signal, were considered. Each of these time series was down-sampled to 260 data points. FIGS. 6C and 6F show the 21 regressors with 0.72 second time shift between the consecutive ones.

NIRS and fMRI Data Analysis

For each subject, both NIRS and fMRI data were analyzed using FEAT, part of the FSL analysis package (FMRIB Expert Analysis Tool, v5.98, on the internet at fmrib.ox-.ac.uk/fsl, Oxford University, UK). fMRI preprocessing steps included motion correction, slice time correction, spatial smoothing and high pass temporal filtering (cut-off frequency=0.02 Hz to remove very slow instrumental drifts).

The only regressor of interest used in these analyses was the $\Delta[HbO]$ obtained from NIRS data collected from the path between the source 540 and the detector 520 at one of the time shifts described above to model the global physiological signal (LFO) observed in BOLD fMRI. Since the $\Delta[HbO]$ represented a real-time measurement of hemodynamics, neither the temporal derivative nor a hemodynamic response function were used. The temporal high pass filter (0.02 Hz) was applied to the regressor for consistency. The motion parameters, estimated from the motion correction preprocessing step on the fMRI data, were included as confounds to further remove motion-correlated noise. A confound is a parameter put into a GLM to account for signal variance not due to the task of interest. For example, if a subject moves their head at certain times during the scan, a term that models such motion of the head can be used as a confound. In general, confounds account for variances due to known disturbances and are used to prevent corruption of the fit.

The GLM was calculated voxel by voxel using FMRIB's improved linear model (FILM) with pre-whitening. Regression coefficients at each voxel were transformed to z statistics indicating the statistical significance of model-related BOLD signal change. The significance threshold at the voxel level was set as $z>2.3$. A cluster threshold of $p<0.05$ was applied to the clusters which survived the local voxel threshold, and the significance of the cluster was computed. The fMRI data were co-registered to the subject's structural scan, and then to the standard MNI152 brain.

This image analysis was repeated 21 times for each of the time shifted copies of the NIRS $\Delta[HbO]$ regressor. The resulting thresholded z-statistic maps were concatenated in time and displayed in sequence as a movie in order to assess the spatial pattern of $\Delta[HbO]$-correlated regions as they changed over time.

The same procedure was applied to the NIRS–$\Delta[Hb]$ regressor. Since the BOLD signal is negatively correlated with $\Delta[Hb]$ (as opposed to being positively correlated with $\Delta[HbO]$), the sign of the regressor was inverted to allow direct comparison of the two analyses.

A total of 42 analyses (21 for $\Delta[HbO]$ regressors and 21 for −$\Delta[Hb]$ regressors) were carried out for the data collected over each of the three paths. The whole procedure was repeated for different subjects.

Results and Discussion

Characteristics of the NIRS Signal

FIGS. 6A, 6B and 6C, show the time traces of $\Delta[HbO]$, its enlarged section, and the 21 regressors of various time shifts (separated by 0.72 s) used in the study, respectively. FIGS. 6D, 6E and 6F show the corresponding graphs for $\Delta[Hb]$.

In general, cerebral blood has a high oxygen saturation, varying from almost 100% in arterial blood to ~60% in venous blood, and a resulting high ratio of [HbO] to [Hb]. FIGS. 6A-F indicate that the $\Delta[HbO]$ signal amplitude (and signal to noise ratio (SNR)) is approximately 3-4 times the size of the $\Delta[Hb]$ (as seen in FIGS. 6B and 6E). Therefore in some cases, $\Delta[HbO]$ is chosen to be the regressor. The time trace of resampled $\Delta[Hb]$ is negatively correlated with that of $\Delta[HbO]$ (as seen in FIGS. 6C and 6F). Therefore, −$\Delta[Hb]$ was used as regressors to generate positive correlations in order to compare with the results from $\Delta[HbO]$.

Figure 7A:
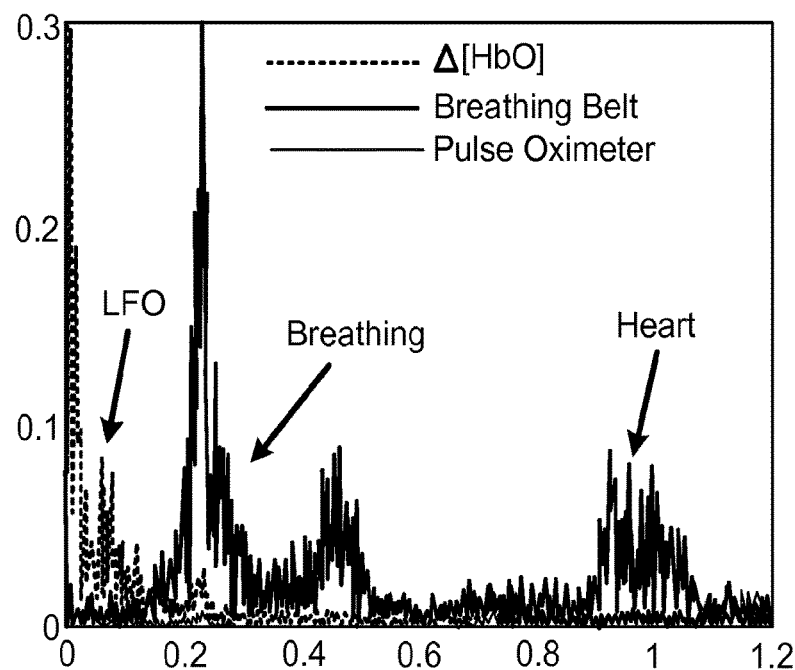
FIGS. 7A and 7B are graphs representing examples of power spectra of oxy-hemoglobin in the blood of a human subject.
Figure 7B:
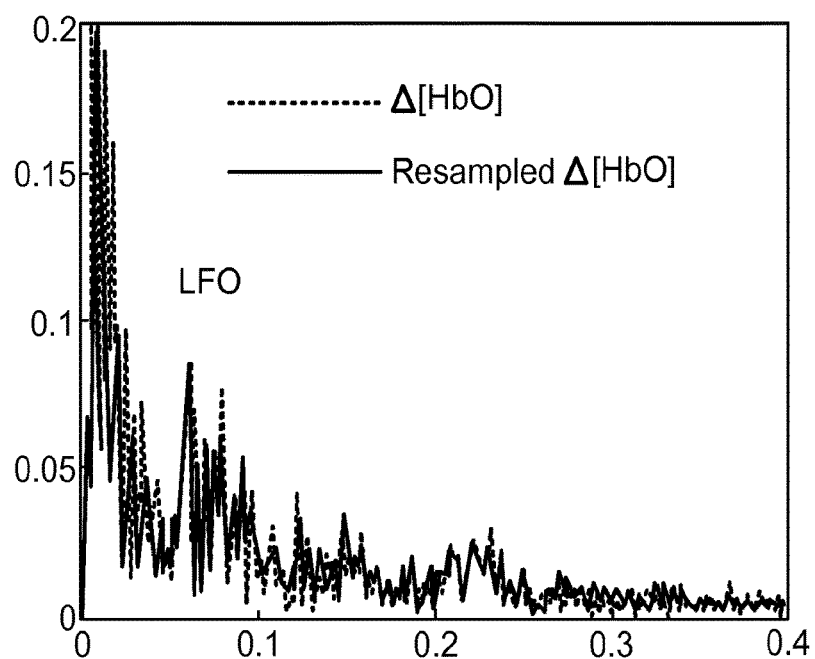

A Fourier analysis was performed on the temporal traces of $\Delta[HbO]$ and the other physiological recordings, including the peripheral pulse signal measured by the finger-tip oximeter and the respiration measured by the breathing belt. FIG. 7A shows the power spectra of the $\Delta[HbO]$ measured with NIRS over a particular path, the peripheral pulse measured with pulse oximeter, and the respiratory belt waveform for a subject. FIG. 7B shows the enlarged view of the frequency spectrum (up to 0.4 Hz) for $\Delta[HbO]$ and its resampled version (after high pass filtering by FEAT at 0.2 Hz).

FIGS. 7A and 7B show a number of results: 1) the cardiac frequencies, as indicated by the data from both the oximeter and NIRS, were in general centered around 1.0 Hz. The cardiac frequency can therefore be a prominent component of the NIRS signal. 2) The respiration frequencies, derived from the breathing belt data, in general, center between 0.2 to 0.4 Hz. In some subjects, a double-peak respiration frequency was also observed. The respiration frequencies are strong components of the NIRS data for some subjects, but not for all subjects. The direct effect of the respiratory waveform on the NIRS data (i.e. at the fundamental respiratory frequency) is relatively small and variable. This does not preclude the possibility that subtle changes in the breathing rate or depth of inhalation might affect the data outside of this band. These effects would likely be part of the LFO signal, and through-space susceptibility effects at the breathing frequencies, can affect the fMRI data without affecting the NIRS signal. 3) The LFOs, at frequencies around and below 0.1 Hz, were prominent in the NIRS data and not observed in either the pulse oximeter or respiratory belt data (although this may be in part due to high pass filtering within the physiological recording system).

FIG. 7B shows that the NIRS data after lowpass filtering and resampling retains only the frequencies <0.35 Hz. The dominant components are below 0.1 Hz. The fMRI data analysis revealed a spatially complex and widespread pattern of voxels (including distinct, bilaterally symmetric clusters) with time courses significantly correlated with the $\Delta[HbO]$ regressor.

Voxels where BOLD Signals Correlate with Time-Shifted $\Delta[HbO]$

Figure 8:
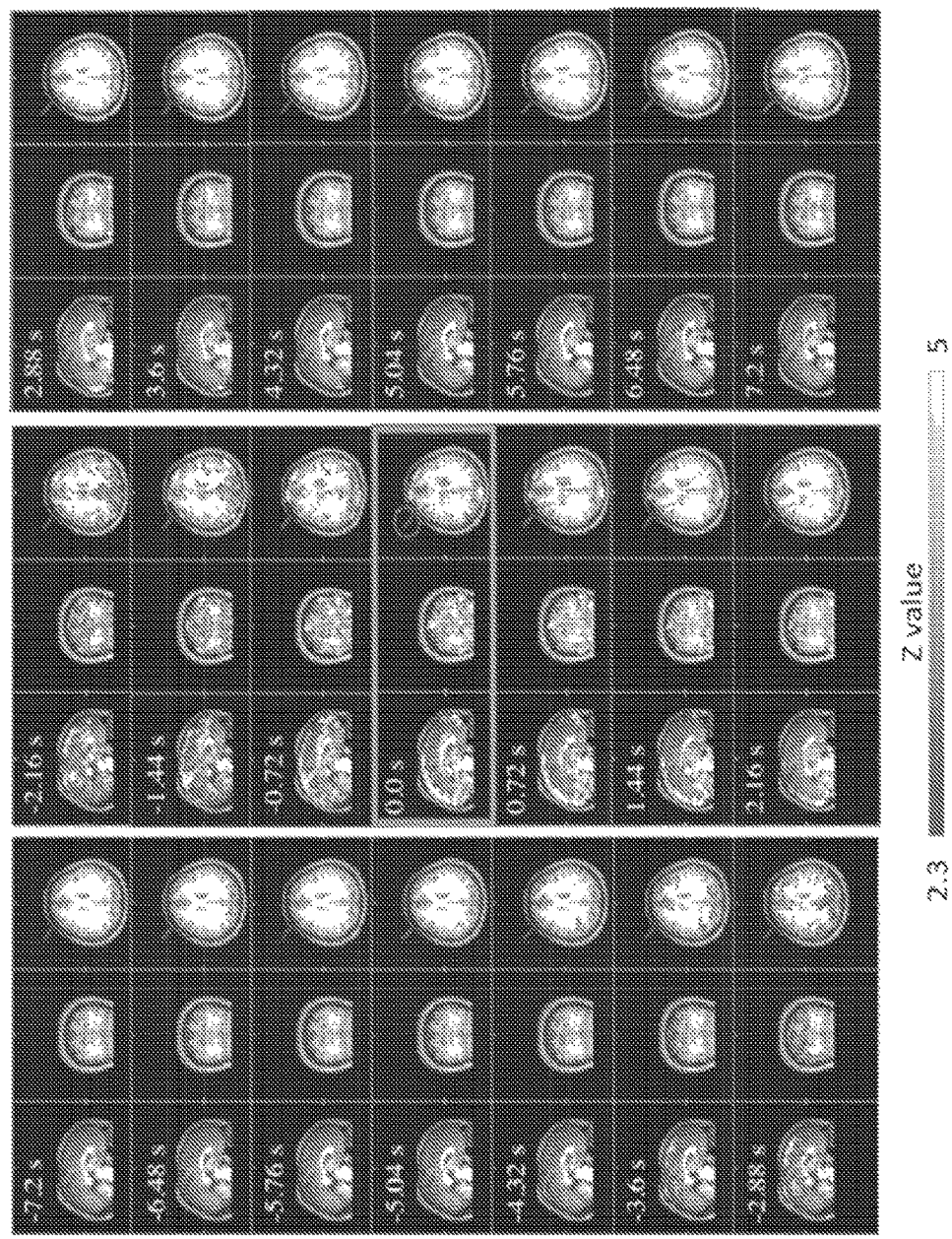
FIG. 8 is a series of z-statistic maps of examples of BOLD fMRI signals.

Twenty-one z-statistic maps of BOLD fMRI signals were calculated, where NIRS-measured $\Delta[HbO]$ traces (shifted from −7.2 to 7.2 seconds in increments of 0.72 seconds), were used as regressors for every subject (the same procedure was applied using the −$\Delta[Hb]$ data). FIG. 8 displays twenty-one z-statistic maps with increments of 0.72 seconds using $\Delta[HbO]$ as regressors for a particular subject. The number on the top left of each graph indicates the time-shift of the regressor for that particular graph. Each z-statistic map was the result of an independent GLM analysis using a different regressor. This was possible because the NIRS recording was longer than the fMRI time series in both directions, and the NIRS signal had temporal resolution as high as 80 ms (acquisition rate of 12.5 Hz). However, because the TR was 1.5 seconds, a time step of 0.72 seconds was sufficient to adequately sample the subtle details of the signal changes over time.

In FIG. 8, the z-statistic maps of activation to the various shifted Δ[HbO] regressors show areas where the BOLD signal is significantly positively correlated with Δ[HbO]. The axial level of the brain was chosen to be at the position that one of the two NIRS probe markers was visible (circled in red in the z-statistic map of no time shift). Instead of being only concentrated underneath the marker, the voxels with time courses modeled by the Δ[HbO] activations were widespread, at a range of depths, and bilaterally symmetrical. As seen from FIG. 8, by performing multiple GLM analyses of the BOLD data using a population of NIRS regressors that have been shifted in time, time-dependent changes in the spatial patterns of significantly NIRS-correlated BOLD signal can be observed throughout the brain. From the sagittal view of the z-maps, the BOLD signal wave starts to appear at locations near the callosomarginal, frontopolar, and parietooccipital arteries.

As time progresses, the wave becomes widespread in the gray matter, as it passes through capillary beds and then retreats towards the venous systems through several paths, including, for example: 1) the superior cerebral vein to the superior sagittal sinus (also visible from the coronal view); 2) the inferior sagittal sinus combining internal cerebral vein to the straight sinus; 3) through the transverse sinus (visible in the coronal view); and 4) through the anterior and posterior spinal veins. The path the wave follows through the brain strongly resembled that of the cerebral vasculature.

Figure 9A:
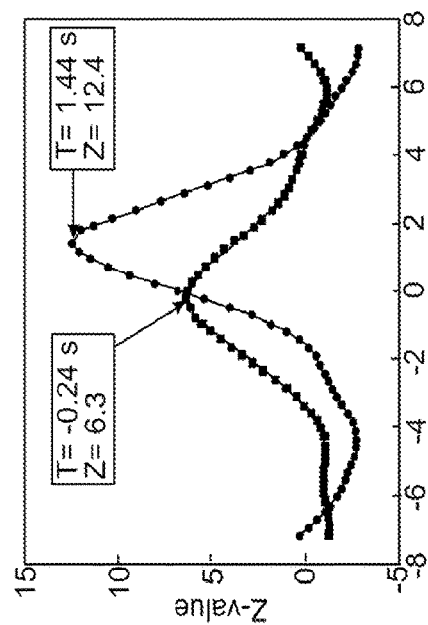
FIGS. 9A-9D are a series of images and graphs that show examples of experimental results.
Figure 9B:
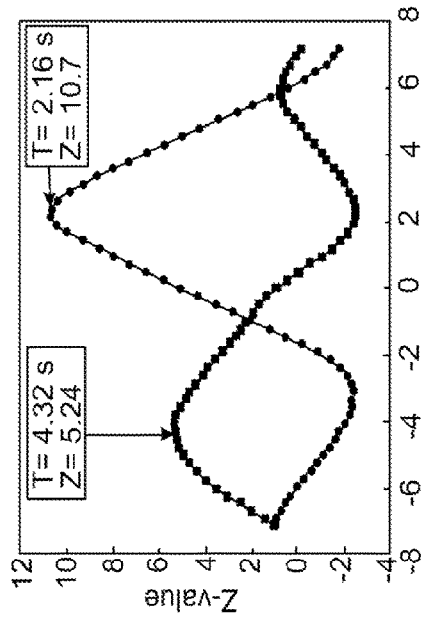

The total time span of the wave's passage through the brain from appearance to disappearance was about 9.36 seconds (−5.04~4.32 seconds) as seen in FIG. 8. However, the maxima of the z values in a given voxel as a function of time shift are quite broad. A more accurate measure of the relative delay of the wave between two voxels can be derived by comparing the time lag of the peak z-value in each voxel. FIGS. 9A and 9B show the position of two voxels and their z-value vs. time shift, respectively. In this analysis, a higher resolution of 0.24 seconds was used in the time shift dimension (from −7.2 to +7.2 seconds) resulting in 61 z values. Both voxels were on the superior sagittal sinus. According to FIG. 9B, the relative times for the peak of the wave to reach the purple circle and green circle are −0.24 seconds and 1.44 seconds respectively, therefore the time it took for the wave to travel from the purple circle to the green was about 1.68 seconds.

Figure 9C:
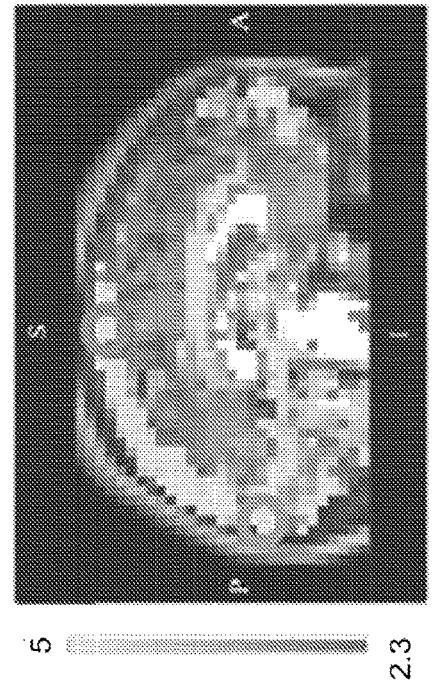
Figure 9D:
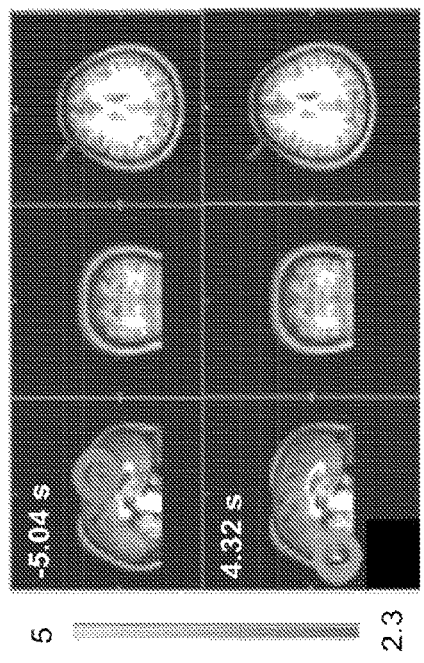

This method was then applied to two activated voxels, which appeared at the beginning (t=−5.04 seconds) and the end (t=4.32 seconds) of the wave's observed passage through the brain, in order to estimate the time for the wave to pass the whole brain. FIG. 9C shows the position of these two voxels and their time of appearance. FIG. 9D shows their z-value vs. time shift. The time for the wave to pass the brain was about 6.48 seconds.

The z-values were observed to be the highest in the venous system (especially superior sagittal sinus and transverse sinus), which is likely due to the fact that these vessels are considerably larger than other brain blood vessels. To further demonstrate this point, a higher threshold of z>4 was applied to the concatenated z-statistic maps in FIG. 8, and the maximum value along the time shift dimension was selected for each voxel to generate a 3-D map. The map was then surface rendered using fslview (part of the FSL package). FIG. 10C shows the result of this combined z-statistic map in a 3-D rendition, together with the 3-D rendering images of the structure brain in FIG. 10A and that of phase contrast angiogram in FIG. 10B. By comparing FIGS. 10B and 10C, the superficial cerebral veins, the superior sagittal sinus, and the transverse sinus can be identified.

Voxels where BOLD Signals Correlate with Time-Shifted −Δ[Hb]

Figure 11:
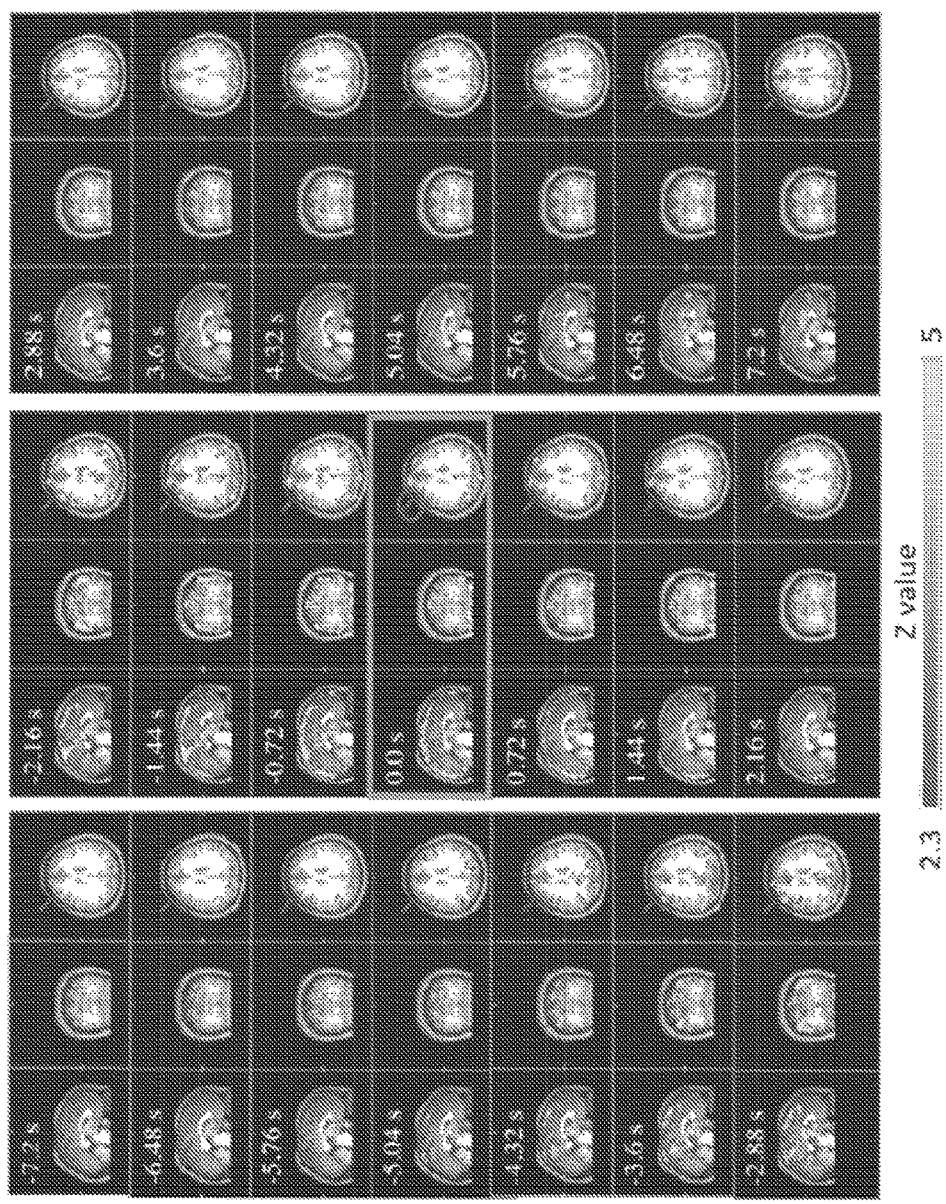
FIG. 11 is a series of z-statistic maps of examples of BOLD fMRI signals.

FIG. 11 shows twenty-one z-statistic maps with increments of 0.72 seconds using −Δ[Hb] as regressors for a particular subject. The results depict similar patterns of activation in each z-statistic map and similar passage of the wave though the brain, when compared to the result of Δ[HbO]. However, the activation maps of −Δ[Hb] had smaller spatial extent. This was likely due to lower the SNR of the −Δ[Hb] measurement compared to Δ[HbO], which results in lower z-values, and fewer voxels exceeding the threshold of 2.3.

The fact that the set of voxels where the BOLD fMRI signal correlates with the NIRS-detected LFOs evolves temporally through the brain indicates that a major component of the LFOs is widely spatially distributed throughout the brain. This distribution altered over time, which was not consistent with a regional vascular origin. Moreover, the temporal evolution of the LFOs appeared to closely follow the cerebral circulatory system from arteries to the gray matter (where most blood vessels reside), to the venous system, which was not consistent with a neural origin. The component of the LFOs that moved with the blood was already present before the blood reached the gray matter and therefore suggested a source outside of the brain.

The present experiment supported the notion that a significant portion of the signal in the low frequency range arises from a non-neuronal source and that the signal confounded the detection of resting-state connectivity networks. The above experiment described identifying and removing this blood-borne noise component which can greatly improve the efficiency of detection of resting-state neural activation.

In some cases, the multimodal NIRS/fMRI correlation time shift imaging may provide a novel contrast mechanism that can be exploited as a tool for characterizing cerebral blood flow directly. When blood in arterial, venous, and capillary compartments all show detectable signals, time shifts between the various regions can be easily determined. In some cases, quantization of other blood flow parameters may also be possible. In general, information can be extracted from typical fMRI datasets without imposing major restrictions on experiment design.

Example 2: Spectral Separation of NIRS Signals

Figures 12A, 12B, 12C, 12D, 12E:
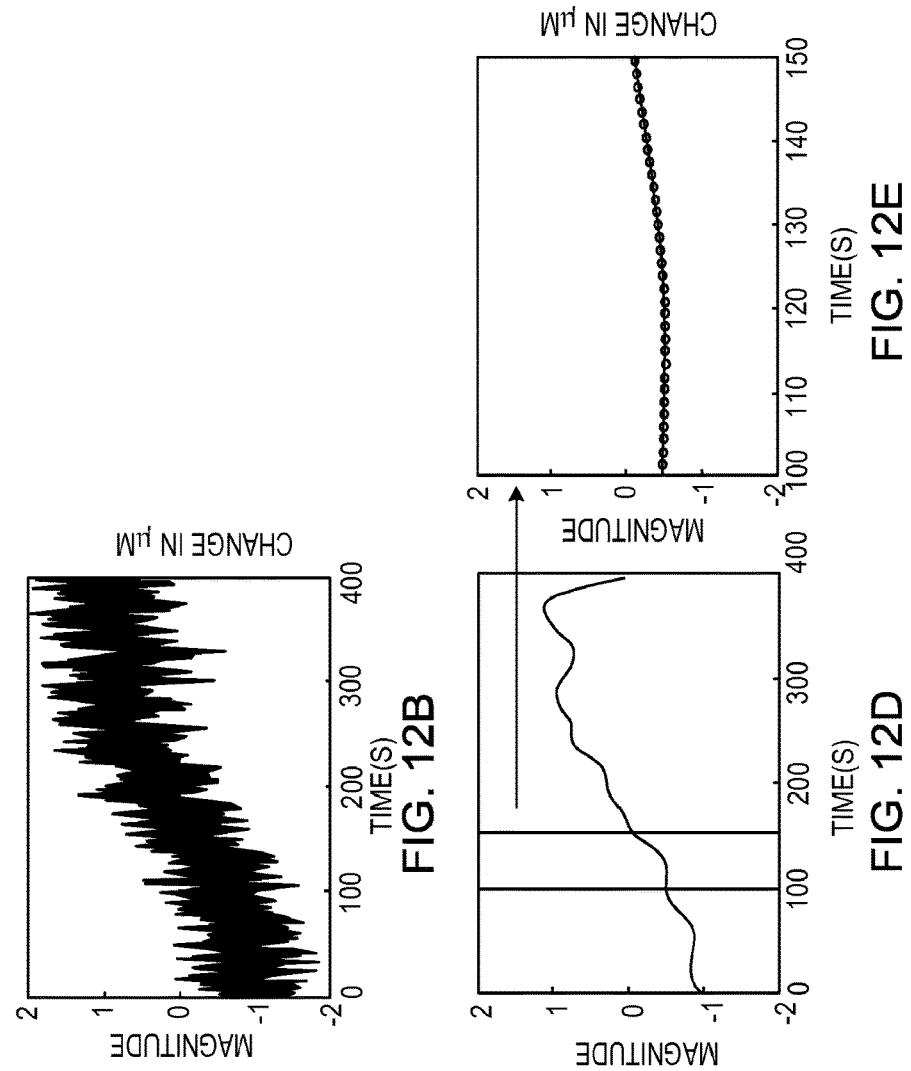
FIGS. 12A to 12N are a series of plots related to examples illustrating separation of NIRS signals into different spectral bands.
Figures 12L, 12M, 12N:
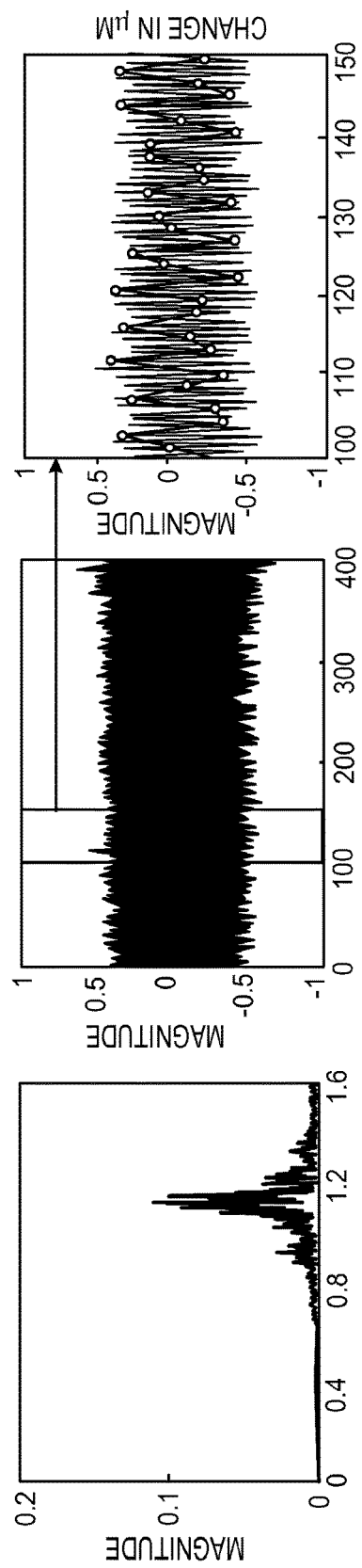

In this example, a temporal trace of NIRS was first spectrally separated into four bands using a zero delay Fourier domain bandpass filter in Matlab. The four bands were defined as very low frequency oscillation (VLF), VLF<0.01 Hz; low frequency Oscillation (LFO), 0.01<LFO<0.1 Hz; respiration (Resp), 0.2<Resp<0.6 Hz; and cardiac pulsation (Card), Card>0.8 Hz. The temporal signal from each band was then resampled according to the TR of the fMRI acquisition. FIG. 12 shows the process for one subject. FIGS. 12a, 12c, 12f, 12i and 12l show the power spectra for (a) original data, (b) VLF, (c) LFO, (d) Resp and (e) Card, respectively. FIGS. 12b, 12d, 12g, 12j and 12m show the corresponding time traces, respectively. FIGS. 12e, 12h, 12k and 12n show the enlarged sections of the corresponding time traces, respectively. The resampled points (separated by 1.5 s) in the enlarged sections are shown as closed circles. Regressor interpolation at progressive time delays can then be applied on each spectrally separated band to assess the spatiotemporal evolutions of VLF, LFO, respiration and cardiac effects in the cerebral blood circulations or the circulations of other body organs.

Example 3: Noise Removal from BOLD Data

The following examples illustrate how some of the factors described herein affect the efficacy of noise removal from BOLD data. In the following examples, different types of NIRS data (deoxy-hemoglobin, $\Delta$[HbR] and total hemoglobin $\Delta$[tHb]) were used alone and in combination with one another, the effect of using a plurality of frequency bands were compared, and data from different NIRS detection paths were compared. The probe placement for the experiment was substantially same as that shown in FIG. 5.

Choice of NIRS Type

Figure 13A:
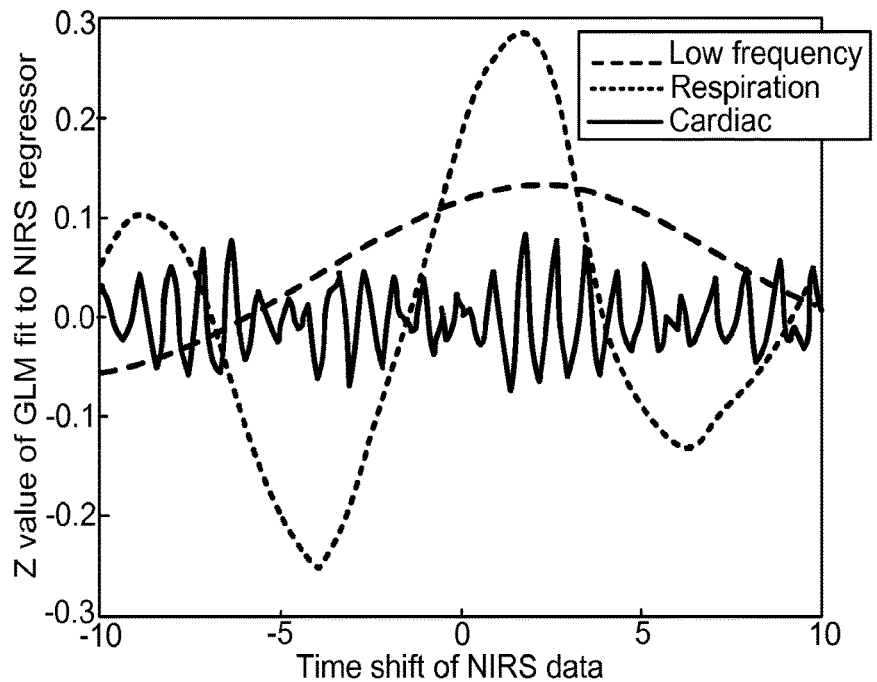
FIGS. 13A and 13B are plots showing correlation between NIRS and BOLD signals.
Figure 13B:
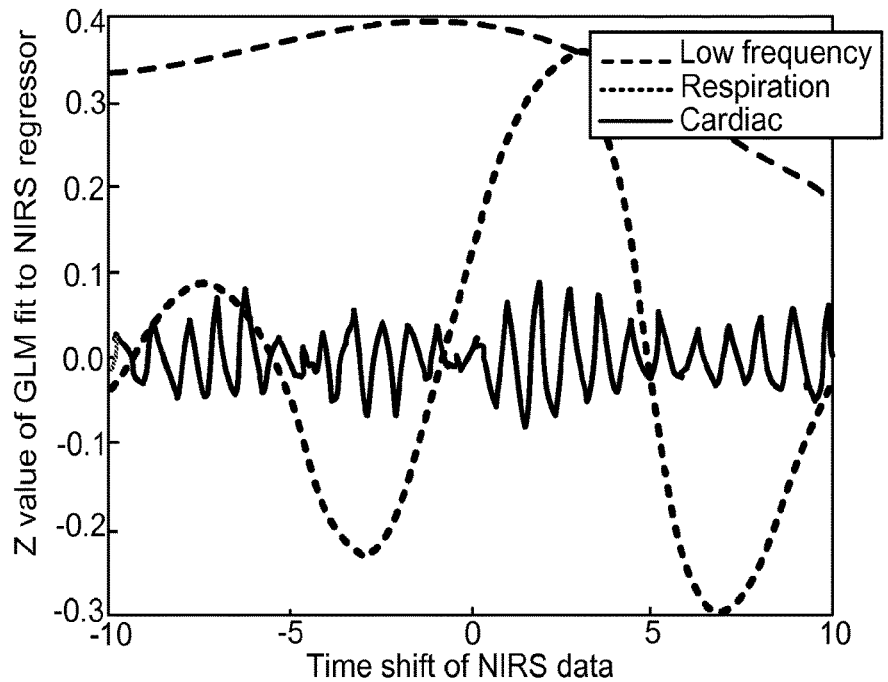

As shown in FIGS. 13A and 13B, two independently determined NIRS quantities −$\Delta$[HbR] and $\Delta$[tHb] were used to illustrate the physiological variation in the BOLD data, and were found to be effective in different areas. For example, the $\Delta$[tHb] regressors worked effectively near large vessels and in gray matter. Because the amount of physiological variance is essentially additive, both types of NIRS signals were used. When regressors were generated from spectrally separated, optimally delayed NIRS signals from short distance NIRS probes, the amount of noise removed using both types was found to be close to the sum of the amount removed using the $\Delta$[HbR] and $\Delta$[tHb] individually.

Spectral Splitting of the NIRS Signal and Optimized Delays

FIG. 14 shows that by performing spectral splitting, and applying separately optimized delays to each band, allowed significant noise removal. FIGS. 14A, 14C and 14E show the results for a short distance between the source and detector and FIGS. 14B, 14D and 14F show the results for a relatively long distance between the source and the detector. In general, FIGS. 14A-14F illustrate the total amount of variance removed by the NIRS regressors. FIGS. 14A and 14B show results for unsplit regressors, FIGS. 14C and 14D show the results for split regressors and FIGS. 14E and 14F show the results for split regressors with optimized time delays. As seen from FIGS. 14A-14F, when both NIRS signals, measured at a short detector distance, were employed, the noise removal appeared to be more effective.

Source Detector Distance

Figure 14A:
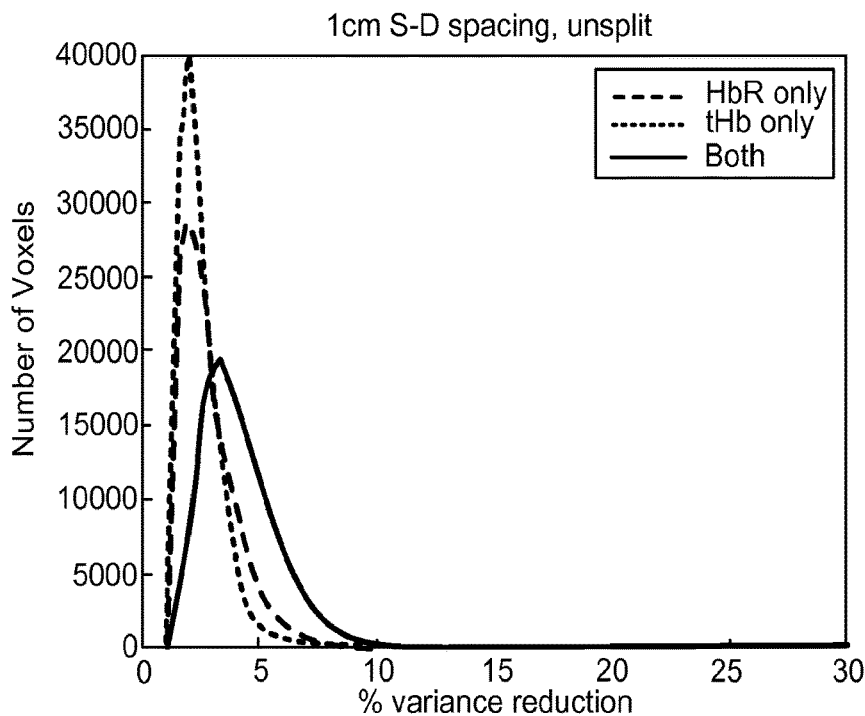
FIGS. 14A-14F are plots illustrating noise reduction examples.
Figure 14B:
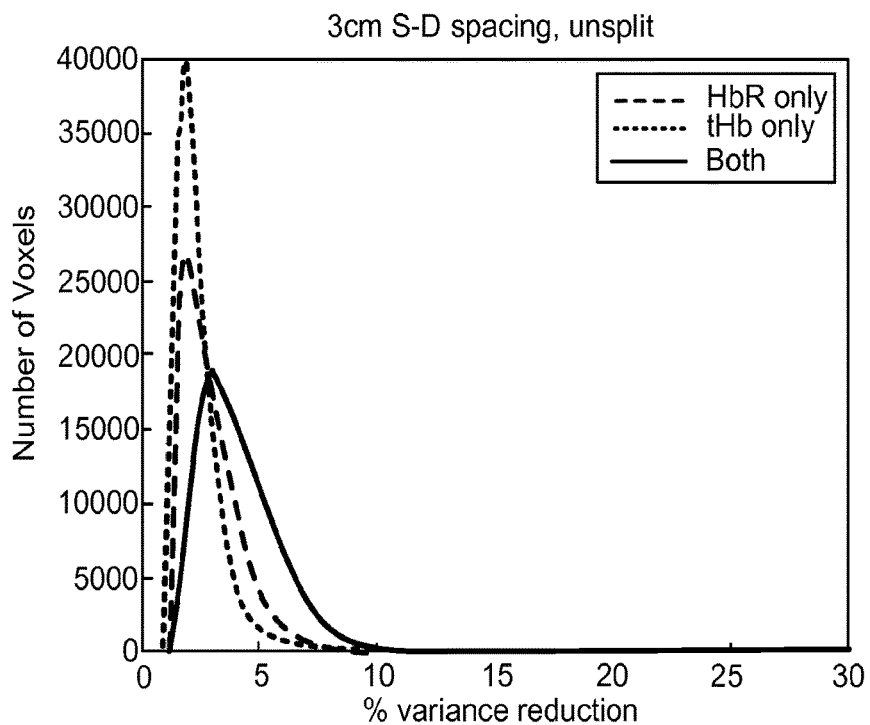
Figure 14C:
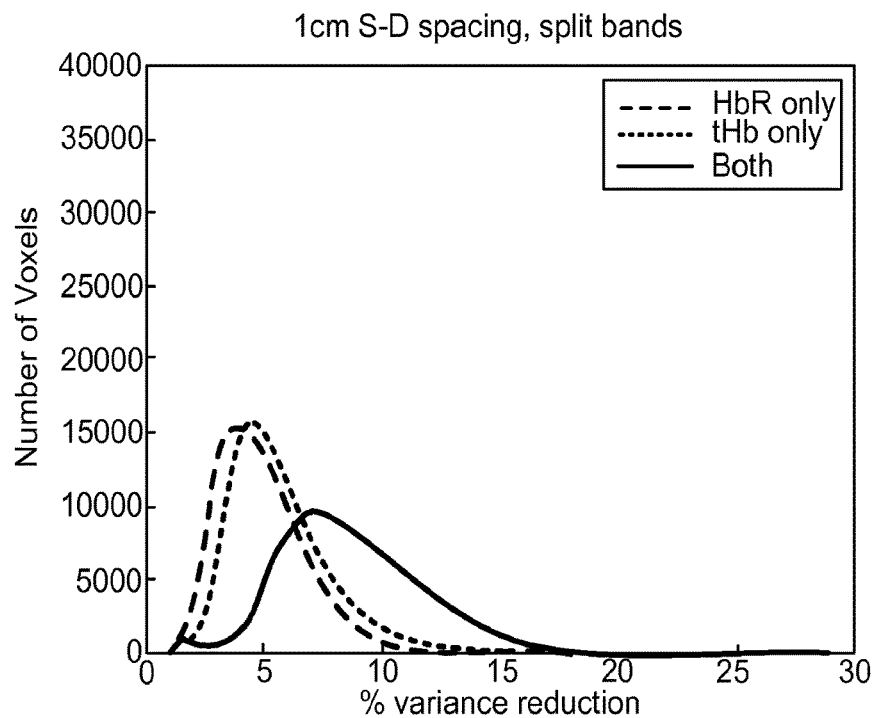
Figure 14D:
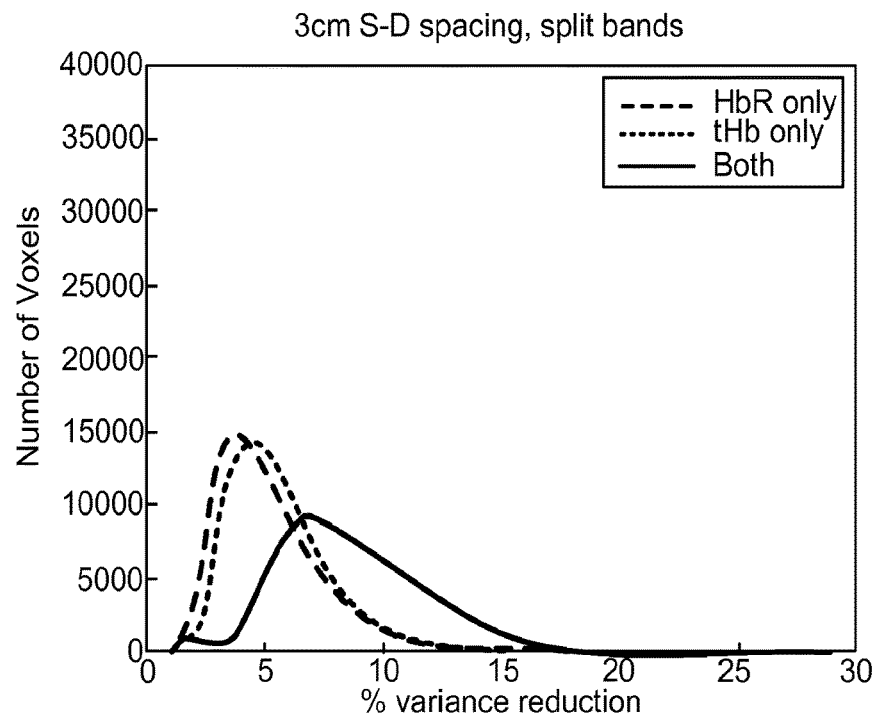
Figure 14E:
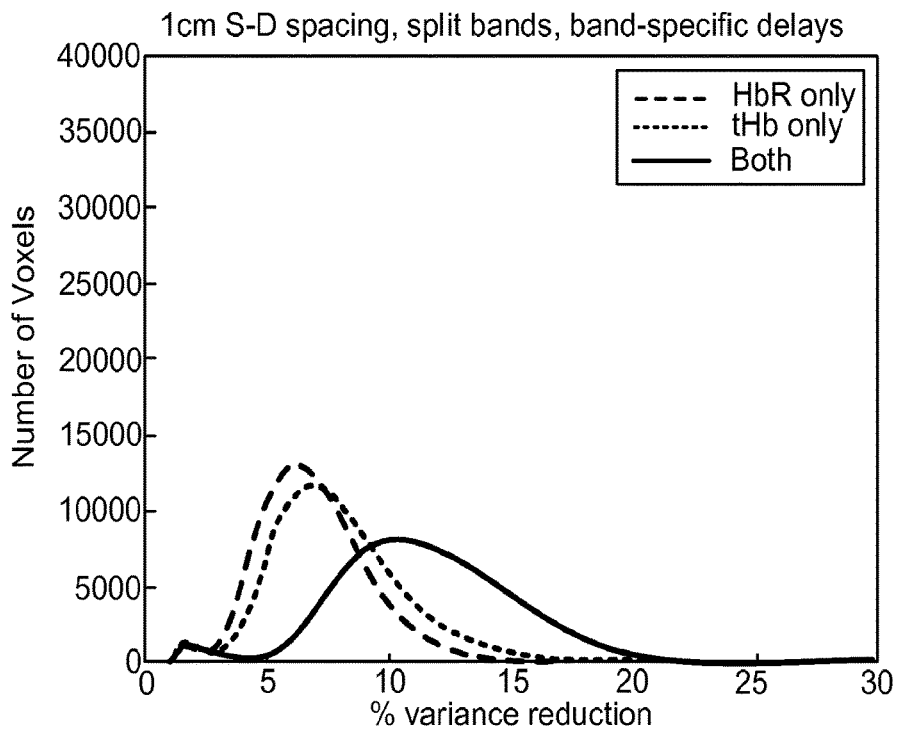
Figure 14F:
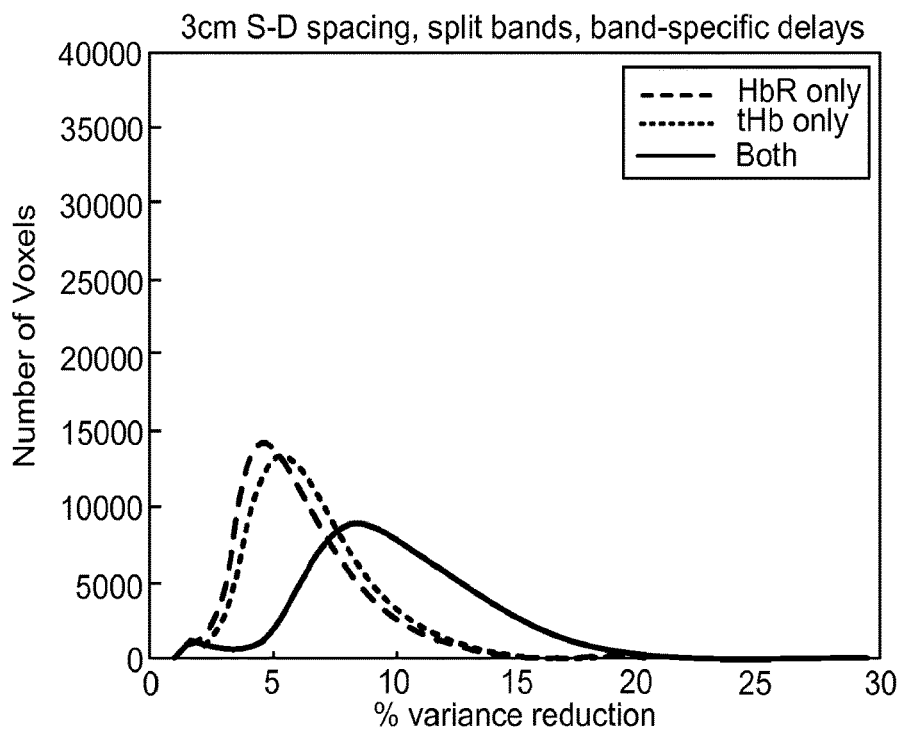

Comparing the left column, i.e. FIGS. 14a, 14c and 14e (1 cm source detector distance) with the right column, i.e. FIGS. 14b, 14d and 14f (3 cm distance) of FIG. 14, it is seen that the amount of noise removed by the more superficial measurement was higher than the amount removed using the probe that received cortical signals (10.53% vs. 8.89% in the case of split regressors). This shows that the signal from the superficial probe is a more accurate representation of the purely physiological blood-borne signal that is being removed. In general, the signal recorded from a probe near the cortex contained a significant amount of hemodynamic variation associated with the cortex itself rather than just blood. In such cases, neural signals from the specific cortical region can contaminate the NIRS signal. In some cases, NIRS data from another body part, such as the fingertip, rather than the same body part (in this case the brain), can be used in the noise removal.

Other Embodiments

Figure 15:
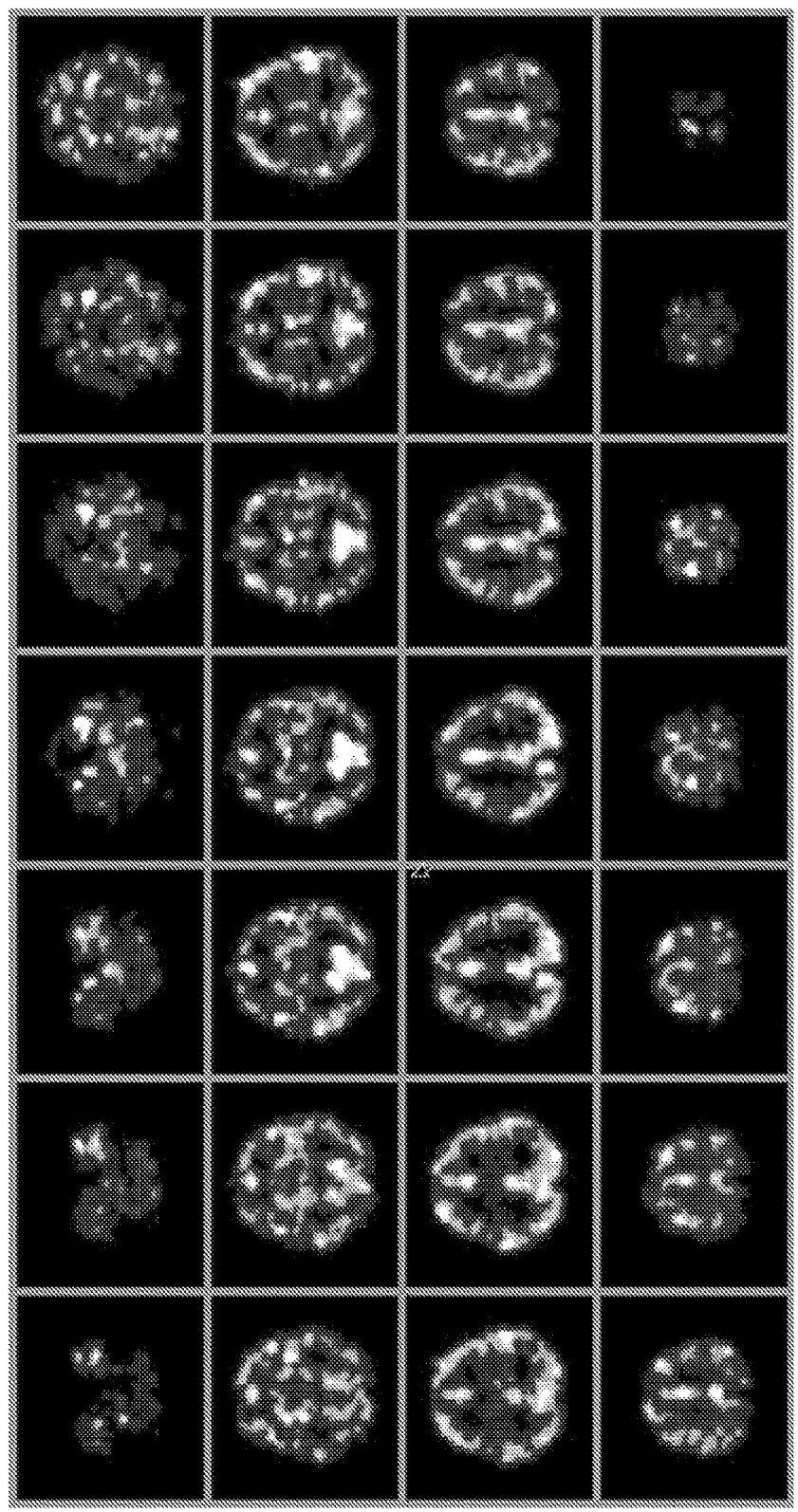
FIG. 15 is an example of a cerebral blood volume (CBV) map

It is to be understood that while the invention has been described in conjunction with the detailed description thereof, the foregoing description is intended to illustrate and not limit the scope of the invention, which is defined by the scope of the appended claims. The methods and systems described herein can be used, for example, where a subject is under controlled respiration. In some implementations, when a subject is holding his breath, the artifacts due to respiration can be minimized to improve the SNR. Also, occasional cued breath holding can be used to improve the estimation of the time delay. Using the methods and systems described herein, blood volume, blood flow speed, blood oxygenation, etc. can be mapped independently. A series of exemplary cerebral blood volume (CBV) maps created using the methods and systems described herein is shown in FIG. 12. The series of CBV images (each at a different time over a predetermined time period) was calculated from a combined fMRI (Siemens 3T, spin echo EPI, TR/TE=1500/30 ms) and 12.5 Hz NIRS $\Delta$[HbO] measurement on the frontal lobe of a subject. The maps in FIG. 15 show how the volume of blood in different regions of a human brain gradually increase and then decrease over a range of time. Other aspects, advantages, and modifications are within the scope of the following claims.

What is claimed is:

1. A computer-implemented method for measuring at least one of blood flow or volume in a subject, the method comprising:
   receiving functional magnetic resonance imaging (fMRI) data that provides information on at least one of volume or oxygenation of blood at one or more locations in a body over a first predetermined length of time;
   receiving spectroscopic measurement data representing at least one of blood concentration or oxygenation at a first portion of the body over a second predetermined length of time;
   deriving, from the fMRI data corresponding to a second portion of the body, a time varying data set representing changes in at least one of blood oxygenation or volume at a second portion of the body over the first predetermined length of time;
   determining a time delay and a value of a similarity metric corresponding to a part of the spectroscopic imaging data that most closely matches the time varying data set, the time delay representing a difference between a first time in which blood flows from a third portion in the body to the first portion and a second time in which blood flows to the second portion from the third portion, and the value of the similarity metric representing an amount of blood at the second portion; and
   determining, based on the time delay and the value of the similarity metric, an estimate of a characteristic of at least one of blood flow or blood volume in the second portion at a given time.

2. The method of claim 1, wherein the fMRI data is acquired from a plurality of fMRI scans performed over the first predetermined time period and at a predetermined frequency.

3. The method of claim 1, wherein the second predetermined length of time includes, and is longer than, the first predetermined length of time.

4. The method of claim 1, further comprising filtering, using a digital or analog filter, the time-varying spectroscopic measurement data to reduce noise.

5. The method of claim 1, wherein determining the time delay further comprises:
   dividing the spectroscopic measurement data into a plurality of segments, each segment corresponding to a particular time shift;

identifying a segment from the plurality of segments that matches the time varying data set derived from the fMRI data from the second portion of the body; and estimating the time delay based on the particular time shift of the identified segment.

6. The method of claim 5, further comprising cross-correlating each segment of the plurality of segments with the time varying data set derived from the fMRI data from the second portion of the body, wherein a peak cross-correlation amplitude represents the value of the similarity metric.

7. The method of claim 5, further comprising performing multiple linear model fits using the plurality of segments.

8. The method of claim 5, wherein a first segment from the plurality of segments partially overlaps a second segment from the plurality of segments.

9. The method of claim 1, further comprising rendering, on a display, the estimated characteristic.

10. The method of claim 1, wherein the estimated characteristic is at least one of an amount of blood and speed of blood flow.

11. The method of claim 1, wherein the first portion of the body at least partially overlaps the second portion of the body.

12. A computer-readable medium storing a computer program for measuring at least one of blood flow or volume, the computer program comprising instructions for causing a computer system to:

receive functional data that provides information on at least one of volume or oxygenation of blood at one or more locations in a body over a first predetermined length of time;

receive near-infrared spectroscopic (NIRS) measurement data representing at least one of blood concentration or oxygenation at a first portion of the body over a second predetermined length of time;

derive, from the functional data corresponding to a second portion of the body, a time varying data set representing changes in at least one of blood oxygenation or volume at a second portion of the body over the first predetermined length of time;

determine a time delay and a value of a similarity metric corresponding to a part of the NIRS measurement data that most closely matches the time varying data set, the time delay representing a difference between a first time in which blood flows from a third portion in the body to the first portion and a second time in which blood flows to the second portion from the third portion, and the value of the similarity metric representing an amount of blood at the second portion; and determine, based on the time delay and the value of the similarity metric, an estimate of a characteristic of at least one of blood flow or blood volume in the second portion at a given time.

13. The computer readable medium of claim 12 wherein the computer system is further caused to:

divide the NIRS measurement into a plurality of segments, each segment corresponding to a particular time shift;

identify a segment from the plurality of segments that matches the time varying data set derived from the functional data from the second portion of the body; and estimate the time delay based on the particular time shift of the identified segment.

14. The method of claim 12, further comprising cross-correlating each segment of the plurality of segments with the time varying data set derived from the functional data from the second portion of the body, wherein a peak cross-correlation amplitude represents the value of the similarity metric.

* * * * *